United States Patent
Segawa

(10) Patent No.: US 11,969,141 B2
(45) Date of Patent: Apr. 30, 2024

(54) MEDICAL DISPLAY CONTROLLING APPARATUS AND DISPLAY CONTROLLING METHOD

(71) Applicant: Sony Olympus Medical Solutions Inc., Tokyo (JP)

(72) Inventor: Kazunori Segawa, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 762 days.

(21) Appl. No.: 16/981,287

(22) PCT Filed: Jan. 29, 2019

(86) PCT No.: PCT/JP2019/002857
§ 371 (c)(1),
(2) Date: Sep. 16, 2020

(87) PCT Pub. No.: WO2019/181212
PCT Pub. Date: Sep. 26, 2019

(65) Prior Publication Data
US 2021/0038342 A1   Feb. 11, 2021

(30) Foreign Application Priority Data
Mar. 23, 2018   (JP) ................................. 2018-056341

(51) Int. Cl.
*A61B 1/00* (2006.01)
*A61B 1/04* (2006.01)
(Continued)

(52) U.S. Cl.
CPC ............ *A61B 1/00004* (2013.01); *A61B 1/04* (2013.01); *A61B 90/37* (2016.02); *A61B 90/50* (2016.02)

(58) Field of Classification Search
CPC ...... A61B 90/37; A61B 90/50; A61B 1/00004
(Continued)

(56) References Cited

U.S. PATENT DOCUMENTS

2009/0259108 A1   10/2009   Miles et al.
2017/0150923 A1    6/2017   Bonfils-Rasmussen

FOREIGN PATENT DOCUMENTS

EP    3293972 A1    3/2018
JP    2004-154255 A    6/2004
(Continued)

OTHER PUBLICATIONS

International Search Report and Written Opinion dated Apr. 23, 2019 for PCT/JP2019/002857 filed on Jan. 29, 2019, 9 pages including English Translation of the International Search Report.

*Primary Examiner* — Nadia A Mahmood
(74) *Attorney, Agent, or Firm* — XSENSUS LLP

(57) ABSTRACT

[Problem to be Solved] Provided are a medical display controlling apparatus and a display controlling method capable of enhancing convenience of medical providers.
[Solution] Provided is a medical display controlling apparatus including: a generating unit configured to generate a three-dimensional model of an observed object based on a right-eye medical captured image and a left-eye medical captured image taken by an imaging device configured to image the observed object; and a display controller configured to cause a display screen to display a combination of the three-dimensional model with a right-eye special light observation image and a left-eye special light observation image, or a combination of the three-dimensional model with biological information acquired from an external biological information acquiring apparatus.

20 Claims, 12 Drawing Sheets

(51) Int. Cl.
*A61B 90/00* (2016.01)
*A61B 90/50* (2016.01)

(58) Field of Classification Search
USPC .............................................. 606/1
See application file for complete search history.

(56) References Cited

FOREIGN PATENT DOCUMENTS

| | | | | |
|---|---|---|---|---|
| JP | 2007-007040 | A | 1/2007 | |
| JP | 2009-189688 | A | 8/2009 | |
| JP | 2010-005017 | A | 1/2010 | |
| JP | 2010516402 | A | 5/2010 | |
| JP | 2011-010128 | A | 1/2011 | |
| JP | 2013-144068 | A | 7/2013 | |
| JP | 2013-531538 | A | 8/2013 | |
| JP | 2013-258627 | A | 12/2013 | |
| JP | 2015531661 | A | 11/2015 | |
| JP | 2015228955 | A | 12/2015 | |
| JP | 2016046780 | A | 4/2016 | |
| JP | 2017205343 | A | 11/2017 | |
| WO | WO-2013073061 | A1 | 5/2013 | |
| WO | WO-2016014444 | A1 * | 1/2016 | ......... A61B 1/00009 |
| WO | WO-2018022940 | A1 | 2/2018 | |

* cited by examiner

FIG.9
A
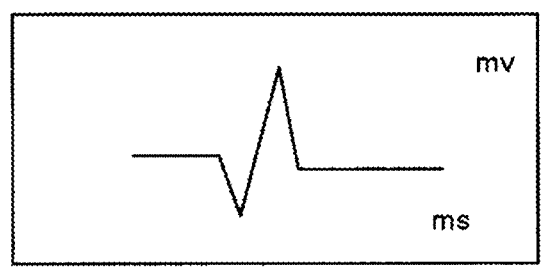
B
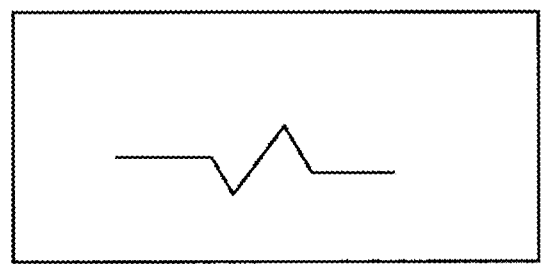
C
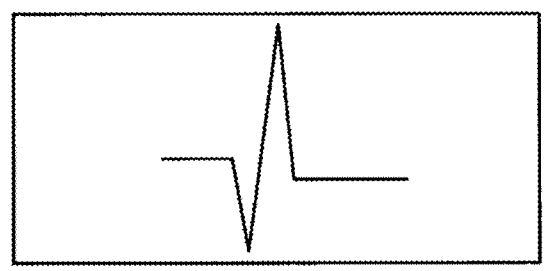
D
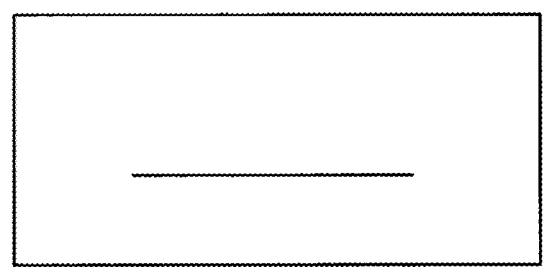

FIG.13
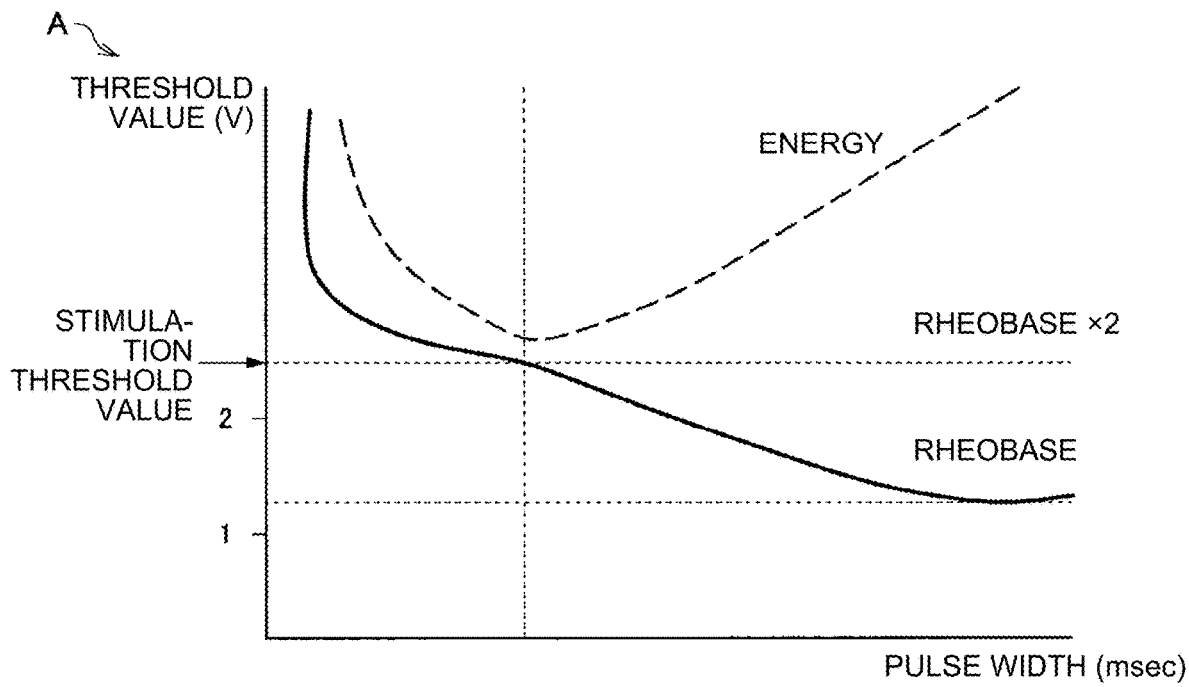
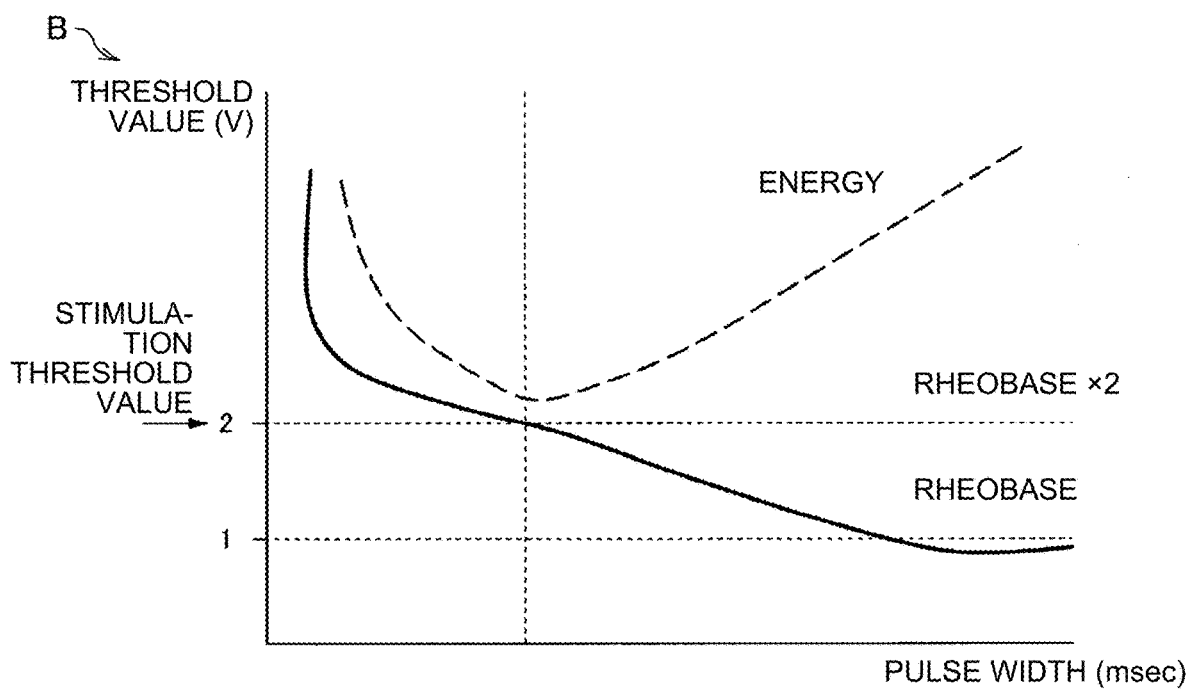

FIG.15
A
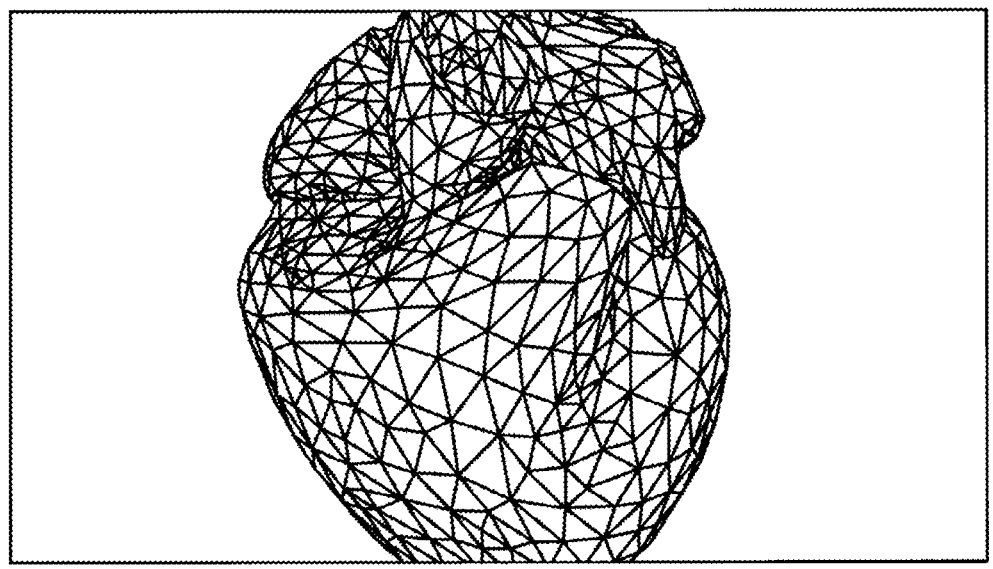
B
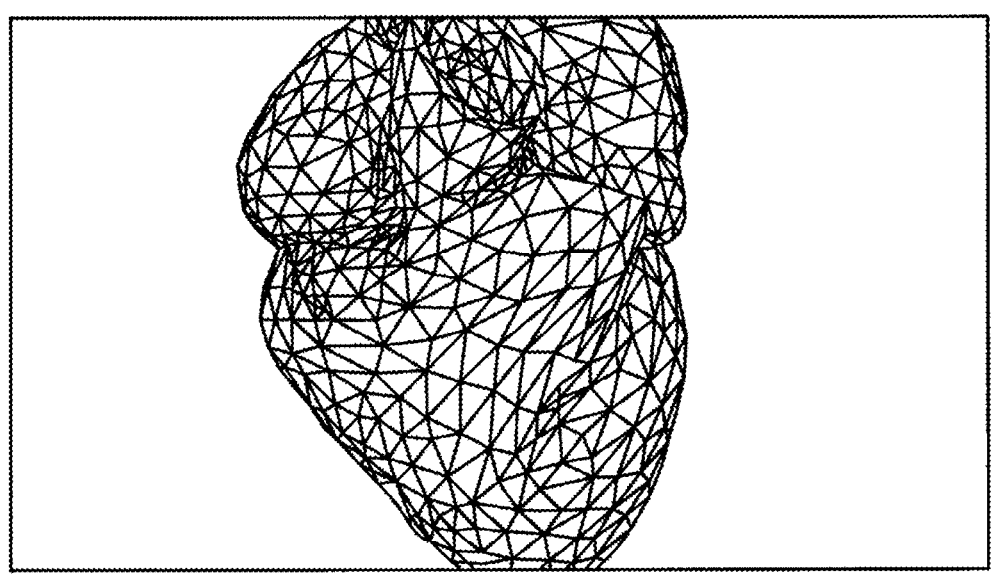

MEDICAL DISPLAY CONTROLLING APPARATUS AND DISPLAY CONTROLLING METHOD

CROSS-REFERENCE TO RELATED APPLICATIONS

The present application is based on PCT filing PCT/JP2019/002857, filed Jan. 29, 2019, which claims priority to JP 2018-056341, filed Mar. 23, 2018, the entire contents of each are incorporated herein by reference.

TECHNICAL FIELD

The present disclosure relate to a medical display controlling apparatus and a display controlling method.

BACKGROUND ART

In recent years, in actual medical settings, medical observation apparatuses that make it possible to observe an enlarged view of an observed object such as a lesion have been used in some situations, for example, for supporting microsurgery such as neurosurgery operations or performing endoscopic surgery. Examples of the medical observation apparatuses include medical observation apparatuses having an optical microscope and medical observation apparatuses having an imaging device that functions as an electronically imaging microscope. Medical observation apparatuses having such an optical microscope will hereinafter be referred to as "optical medical observation apparatuses". In contrast, medical observation apparatuses having such an imaging device may hereinafter be referred to as "electronically imaging medical observation apparatuses" or simply "medical observation apparatuses". Further, a captured image (a moving image or a still image; the same applies hereinafter) taken of an observed object by an imaging device included in a medical observation apparatus will hereinafter be referred to as a "medical captured image".

Due to improvements in the image quality of imaging devices and improvements in the image quality of display devices that display the captured images, electronically imaging medical observation apparatuses have become capable of achieving image quality equal to or higher than that of optical medical observation apparatuses. Further, users (e.g., medical providers such as practitioners and assistants to the practitioners; the same applies hereinafter) who use electronically imaging medical observation apparatuses are able to move the position of the imaging device more freely than when using optical medical observation apparatuses, because there is no need to look through an ocular lens of an optical microscope. For this reason, using electronically imaging medical observation apparatuses has an advantage of being able to support microsurgery and the like with higher flexibility. Electronically imaging medical observation apparatuses are therefore more and more widely used in actual medical settings.

Further, techniques have been developed in relation to "surgery assisting systems configured to manage an apparatus used in an operating room during surgery, from a location away from the operating room". Examples of this technique include techniques disclosed in Patent Document 1 listed below.

CITATION LIST

Patent Literature

Patent Literature 1: Japanese Patent Application Laid-open No. 2007-7040

DISCLOSURE OF INVENTION

Technical Problem

Electronically imaging medical observation apparatuses are capable of performing imaging processes by using light in a specific wavelength band different from that of natural light such as, for example, light in a near-infrared wavelength band or light in a fluorescence wavelength band for fluorescence observation using 5-Aminolevulinic Acid (5-ALA). In the following sections, light in a specific wavelength band different from that of natural light will be referred to as "special light".

When imaging processes are performed by using special light, medical providers such as practitioners and assistants, for example, are able to identify the position of a blood vessel or a tumor in an observed object more easily than when imaging processes are performed by using natural light. However, medical captured images acquired from imaging processes using special light may have much dark noise due to insufficient levels of brightness and/or contrast. When a medical captured image that has been acquired has much dark noise due to insufficient levels of brightness and/or contrast as described herein, there is a possibility that the medical provider may not be able to easily identify the position of the blood vessel or the tumor in the observed object. A medical captured image acquired through an imaging process using special light will hereinafter be referred to as a "special light observation image".

In actual medical settings, for example, "medical apparatuses capable of acquiring biological information such as nerve monitoring apparatuses and nerve stimulation apparatuses configured to electrically stimulate the vagus nerve" are used, in addition to medical observation apparatuses such as electronically imaging medical observation apparatuses. Medical apparatuses capable of acquiring biological information will hereinafter be referred to as "biological information acquiring apparatuses".

The content of the biological information acquired by the biological information acquiring apparatuses are, for example, displayed on an arbitrary display device provided in the actual medical setting. Medical providers such as practitioners and assistants perform medical procedures such as manipulations, by putting together, in their heads, the state of the observed object being observed by a medical observation apparatus with the content of the biological information. For this reason, medical providers may feel burdened in some situations.

The present disclosure will propose a medical display controlling apparatus and a display controlling method being novel and improved that are capable of enhancing the convenience of medical providers.

Solution to Problem

According to the present disclosure, there is provided a medical display controlling apparatus including: a generating unit configured to generate a three-dimensional model of an observed object based on a right-eye medical captured image and a left-eye medical captured image taken by an imaging device configured to image the observed object; and a display controller configured to cause a display screen to display: a combination of the three-dimensional model and a right-eye special light observation image and a left-eye special light observation image; or a combination of the three-dimensional model and biological information acquired from an external biological information acquiring apparatus.

Moreover, according to the present disclosure, there is provided a display controlling method implemented by a medical display controlling apparatus, the display controlling method including: generating a three-dimensional model of an observed object based on a right-eye medical captured image and a left-eye medical captured image taken by an imaging device configured to image the observed object; and causing a display screen to display a combination of the three-dimensional model and a right-eye special light observation image and a left-eye special light observation image, or causing the display screen to display a combination of the three-dimensional model with biological information acquired from an external biological information acquiring apparatus.

Advantageous Effects of Invention

According to the present disclosure, it is possible to enhance the convenience of medical providers.

The abovementioned advantageous effects are not necessarily restrictive. Together with or in place of the abovementioned advantageous effects, any of the other advantageous effects indicated in the present description or any other advantageous effect that can be derived from the present description may be exerted.

BRIEF DESCRIPTION OF DRAWINGS

FIG. 9 is an explanatory drawing for explaining another example of the biological information acquiring process performed by the nerve monitoring apparatus.

FIG. 13 is an explanatory drawing for explaining an example of a biological information acquiring process performed by a nerve stimulation apparatus.

FIG. 15 is an explanatory drawing illustrating an example of processes related to the third application example of the display controlling method according to the present embodiment.

BEST MODE FOR CARRYING OUT THE INVENTION

Figure 1:
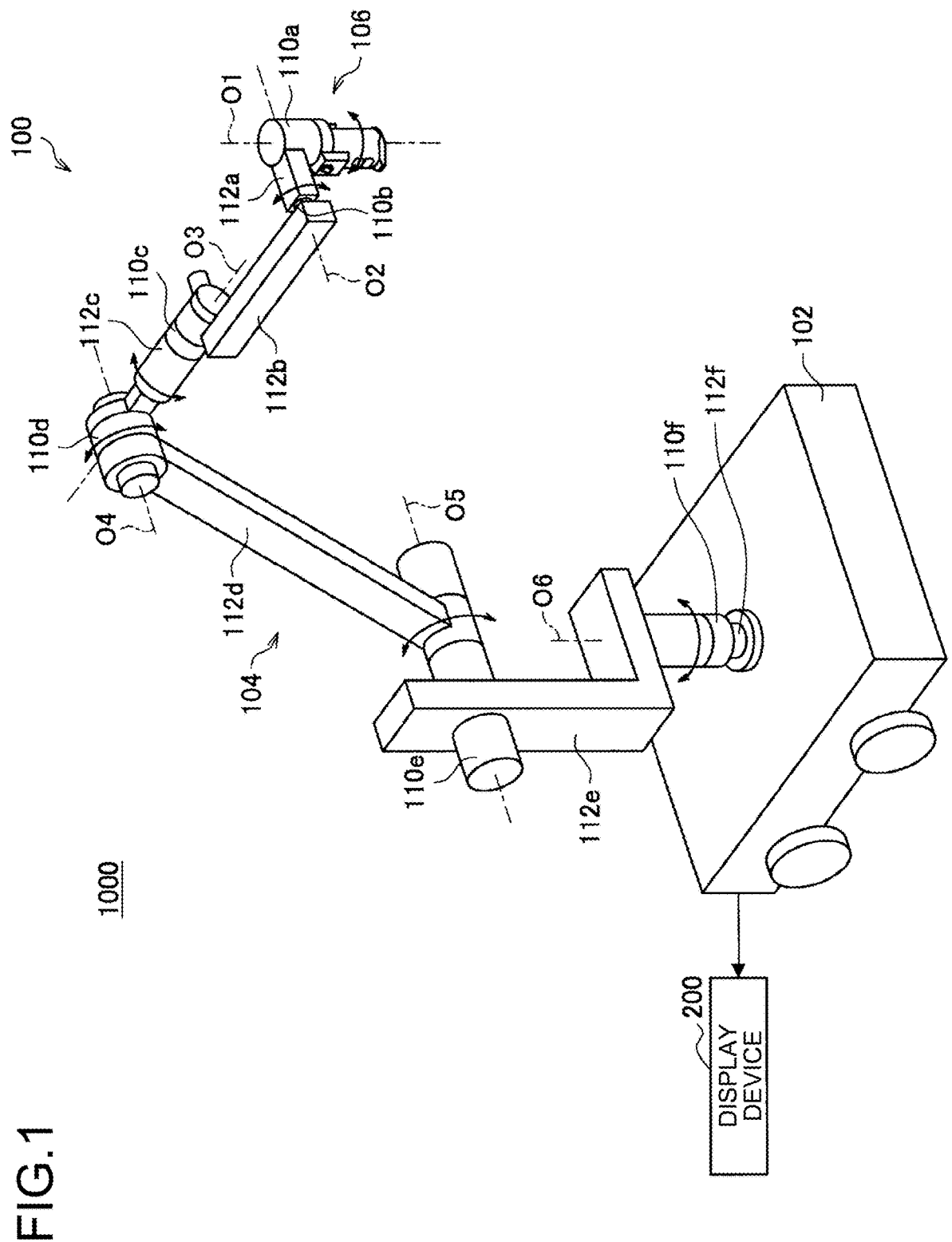
FIG. 1 is an explanatory drawing illustrating a first example of a configuration of a medical observation system according to an embodiment.

Preferred embodiments of the present disclosure will be explained in detail, with reference to the accompanying drawings. In the present description and drawings, some of the constituent elements having substantially the same functional configuration as one another will be referred to by using the same reference characters, and duplicate explanations thereof will be omitted.

The present disclosure will be explained below in the following order:

1. A medical observation system according to the present embodiment and a display controlling method according to the present embodiment
 [1] Configurations of medical observation systems
  [1-1] A medical observation system according to a first example
  [1-2] A medical observation system according to a second example [1-3] A functional configuration of a medical observation apparatus
 [2] A display controlling method according to the present embodiment
 [3] Application examples of the display controlling method according to the present embodiment
  [3-1] A first application example of the display controlling method according to the present embodiment
  [3-2] A second application example of the display controlling method according to the present embodiment
  [3-3] A third application example of the display controlling method according to the present embodiment
 [4] Examples of advantageous effects achieved by using the display controlling method according to the present embodiment
2. A computer program according to the present embodiment
 <A medical observation system according to the present embodiment and a display controlling method according to the present embodiment>

With the description of an example of a medical observation system according to the present embodiment, a display controlling method according to the present embodiment will be explained.

The following will primarily describe an example in which a medical observation apparatus according to the present embodiment performs processes related to a display controlling method according to the present embodiment, i.e., an example in which the medical observation apparatus according to the present embodiment functions as a medical display controlling apparatus. In this situation, possible examples of the apparatus that functions as a medical display controlling apparatus in the medical observation system according to the present embodiment are not limited to the medical observation apparatus according to the present embodiment. For example, in the medical observation system according to the present embodiment, the display device explained later may function as the medical display controlling apparatus configured to perform the processes related to the display controlling method according to the present embodiment. As another example, in the medical observation system according to the present embodiment, an arbitrary apparatus (e.g., a medical controller) capable of performing the processes related to the display controlling method according to the present embodiment may function as the medical display controlling apparatus.

[1] Configurations of medical observation systems

[1-1] A medical observation system according to a first example

FIG. 1 is an explanatory drawing illustrating a first example of a configuration of a medical observation system 1000 according to the present embodiment. For example, the medical observation system 1000 illustrated in FIG. 1 includes a medical observation apparatus 100 and a display device 200.

The medical observation system according to the first example is not limited to the example illustrated in FIG. 1.

For example, the medical observation system according to the first example may further include a medical controlling apparatus (not illustrated) configured to control various types of operations of the medical observation apparatus 100. For the medical observation system 1000 illustrated in FIG. 1, an example is illustrated in which, as a result of the medical observation apparatus 100 including a control unit (explained later), the medical observation apparatus 100 has functions of a medical controlling apparatus (not illustrated), as explained later.

Examples of the medical controlling apparatus (not illustrated) include a "medical controller" and a "computer such as a server". Alternatively, the medical controlling apparatus (not illustrated) may be, for example, an Integrated Circuit (IC) that can be incorporated in any of the abovementioned devices.

Further, the medical observation system according to the first example may be configured to include two or more medical observation apparatuses 100 and/or two or more display devices 200. When two or more medical observation apparatuses 100 are included, the processes related to the display controlling method explained later are performed in each of the medical observation apparatuses 100. Further, when the medical observation system according to the first example includes two or more medical observation apparatuses 100 and two or more display devices 200, the medical observation apparatuses 100 and the display devices 200 may be kept in one-to-one correspondence with each other, or two or more medical observation apparatuses 100 may be kept in correspondence with each display device 200. When two or more medical observation apparatuses 100 are kept in correspondence with each display device 200, the display device 200 is, as a result of receiving a switching operation or the like for example, capable of switching among medical captured images taken by the medical observation apparatuses 100 so as to be displayed on a display screen thereof.

Figure 2:
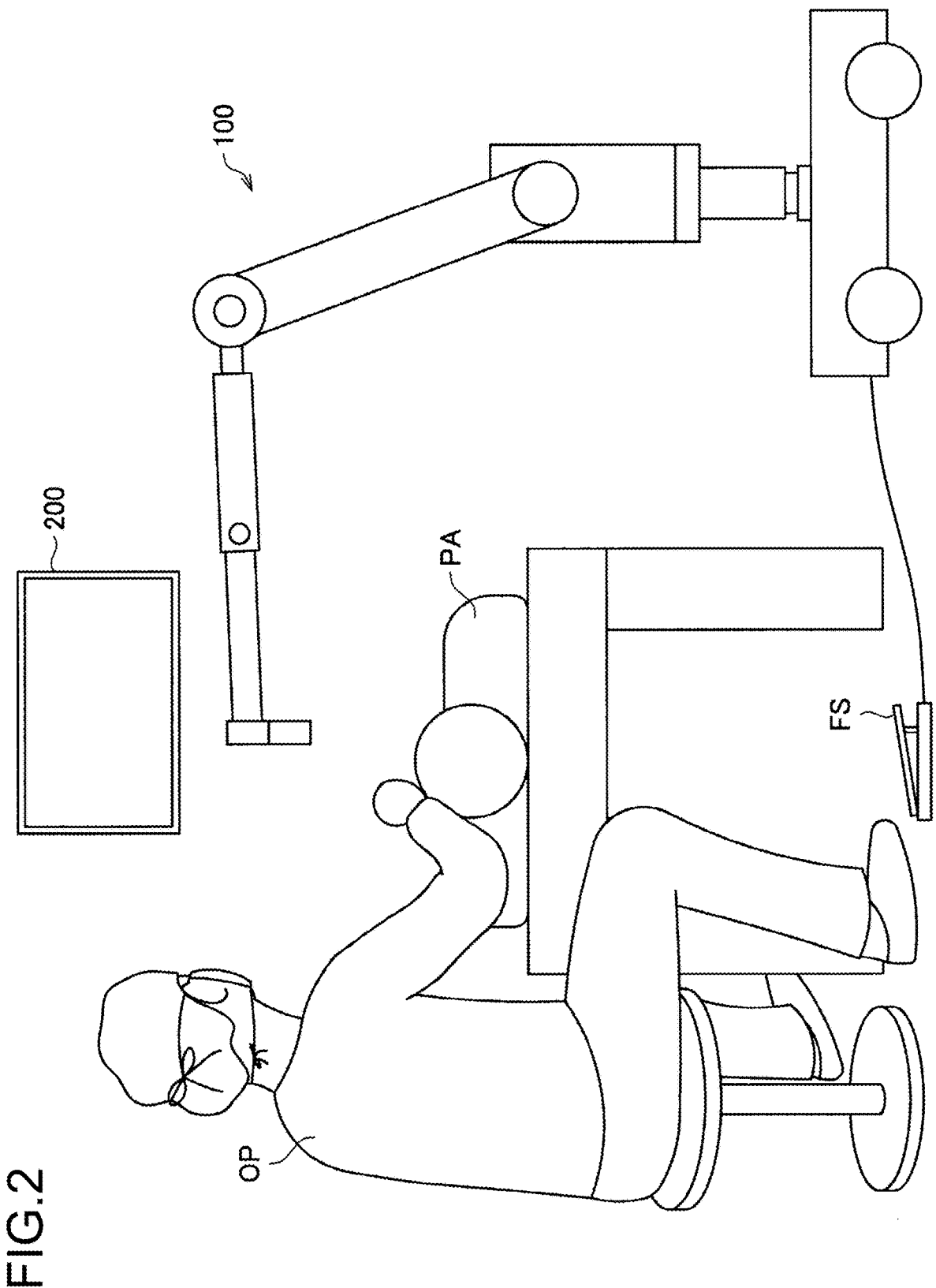
FIG. 2 is an explanatory drawing illustrating an example of a use case that uses the medical observation system according to the present embodiment.

FIG. 2 is an explanatory drawing illustrating an example of a use case that uses the medical observation system 1000 according to the present embodiment and illustrates the example of the use case that uses the medical observation system 1000 according to the first example.

An imaging device (explained later) included in the medical observation apparatus 100 is configured to image a patient PA serving as an observed object (a patient subject to a medical procedure). A captured image taken of the patient subject to the medical procedure corresponds to an example of the medical captured image.

The medical captured image taken by the medical observation apparatus 100 is displayed on a display screen of the display device 200. Further, a practitioner OP (an example of a user of the medical observation apparatus 100) who performs a medical procedure by using the medical observation apparatus 100 performs the medical procedure on the patient PA while viewing the medical captured image displayed on the display screen of the display device 200.

Further, by operating an operation device (e.g., a foot switch FS) external to the medical observation apparatus 100 or an operation device (explained later) included in the medical observation apparatus 100, the practitioner OP brings an arm (explained later) and the imaging device (explained later) included in the medical observation apparatus 100 into operation, so as to bring the medical observation apparatus 100 into a desired state.

Next, devices structuring the medical observation system 1000 according to the first example illustrated in FIG. 1 will be explained.

[1-1-1] The display device 200

The display device 200 is a display means in the medical observation system 1000 according to the first example and corresponds to a display device external to the medical observation apparatus 100. For example, the display device 200 is configured to display, on a display screen, various images such as the medical captured image taken by the medical observation apparatus 100 and an image related to a User Interface (UI). Further, the display device 200 may be configured to be able to realize three-dimensional (3D) display by using an arbitrary scheme. The display of the display device 200 is controlled, for example, by the medical observation apparatus 100 or a medical controlling apparatus (not illustrated).

In the medical observation system 1000, the display device 200 is installed in an arbitrary location in an operating room such as on a wall, the ceiling, the floor, or the like of the operating room, so as to be visible to persons involved in the surgery such as the practitioner.

Examples of the display device 200 include a liquid crystal display device, an organic Electro-Luminescence (EL) display device, and a Cathode Ray Tube (CRT) display device.

The display device 200 is not limited to the examples above. For instance, the display device 200 may be an arbitrary wearable device such as a head mounted display or an eyewear-type device that can be used while being attached to the body of the practitioner or the like.

For example, the display device 200 is driven with electric power supplied from an internal power source such as a battery included in the display device 200 or with electric power supplied from an external power source connected thereto.

[1-1-2] The medical observation apparatus 100

The medical observation apparatus 100 illustrated in FIG. 1 is an electronically imaging medical observation apparatus. For example, when the medical observation apparatus 100 illustrated in FIG. 1 is used for surgery, the practitioner (an example of a user of the medical observation apparatus 100) observes a surgery site (a lesion) while viewing a medical captured image taken by the medical observation apparatus 100 and displayed on a display screen of the display device 200, so as to perform, on the surgery site, various types of procedures such as a manipulation corresponding to a surgery scheme.

As illustrated in FIG. 1, the medical observation apparatus 100 includes, for example, a base 102, an arm 104, and an imaging device 106.

Further, although not illustrated in FIG. 1, the medical observation apparatus 100 may include, for example, one or more processors (not illustrated) configured by using an arithmetic circuit such as a Micro Processing Unit (MPU), as well as a Read-Only Memory (ROM; not illustrated), a Random Access Memory (RAM; not illustrated), a recording medium (not illustrated), and a communication device (not illustrated). For example, the medical observation apparatus 100 is driven with electric power supplied from an internal power source such as a battery included in the medical observation apparatus 100 or with electric power supplied from an external power source connected thereto.

The one or more processors (not illustrated) function as a control unit of the medical observation apparatus 100. The ROM (not illustrated) is configured to store therein programs used by the processors (not illustrated) and controlling-purpose data such as computation parameters. The RAM (not illustrated) is configured to temporarily store therein programs executed by the processors (not illustrated) and the like.

The recording medium (not illustrated) functions as a storage unit (not illustrated) of the medical observation apparatus 100. The recording medium (not illustrated) is configured to store therein, for example, various types of data such as data related to the display controlling method according to the present embodiment and various types of applications. In this situation, examples of the recording medium (not illustrated) include a magnetic recording medium such as a hard disk and a non-volatile memory such as a flash memory. Further, the recording medium (not illustrated) may be detachably attached to the medical observation apparatus 100.

The communication device (not illustrated) is a communication means included in the medical observation apparatus 100 and plays the role of communicating with external devices such as the display device 200 in a wireless or wired manner. In this situation, examples of the communication device (not illustrated) include an IEEE 802.15.1 port with a transmission/reception circuit (wireless communication), an IEEE 802.11 port with a transmission/reception circuit (wireless communication), a communication antenna with a radio frequency (RF) circuit (wireless communication), and a Local Area Network (LAN) terminal with a transmission/reception circuit (wired communication).

[1-1-2-1] The base 102

The base 102 is a base of the medical observation apparatus 100. The base 102 has one end of the arm 104 connected thereto and is configured to support the arm 104 and the imaging device 106.

Further, for example, the base 102 is provided with casters, so that the medical observation apparatus 100 is in contact with the floor surface via the casters. As being provided with the casters, the medical observation apparatus 100 is able to easily move around on the floor surface with the casters.

[1-1-2-2] The arm 104

The arm 104 is configured by connecting a plurality of links to one another with joint parts.

Further, the arm 104 is configured to support the imaging device 106. The imaging device 106 supported by the arm 104 is able to move three-dimensionally. After the imaging device 106 is moved, the position and the posture thereof are held by the arm 104.

More specifically, for example, the arm 104 is configured with a plurality of joint parts 110*a*, 110*b*, 110*c*, 110*d*, 110*e*, and 110*f*; and a plurality of links 112*a*, 112*b*, 112*c*, 112*d*, 112*e*, and 112*f* that are rotatably connected to one another by the joint parts 110*a*, 110*b*, 110*c*, 110*d*, 110*e*, and 110*f*. The rotatable range of each of the joint parts 110*a*, 110*b*, 110*c*, 110*d*, 110*e*, and 110*f* is arbitrarily set at a designing stage or a manufacturing stage, so as to realize desirable motion of the arm 104.

In other words, in the medical observation apparatus 100 illustrated in FIG. 1, six degrees of freedom are realized for moving of the imaging device 106, by six rotation axes (a first axis O1, a second axis O2, a third axis O3, a fourth axis O4, a fifth axis O5, and a sixth axis O6) corresponding to the six joint parts 110*a*, 110*b*, 110*c*, 110*d*, 110*e*, and 110*f* structuring the arm 104. More specifically, in the medical observation apparatus 100 illustrated in FIG. 1, the moving with the six degrees of freedom are realized, namely three degrees of freedom for translation and three degrees of freedom for rotation.

Each of the joint parts 110*a*, 110*b*, 110*c*, 110*d*, 110*e*, and 110*f* is provided with an actuator (not illustrated). As being driven by the actuator (not illustrated), each of the joint parts 110*a*, 110*b*, 110*c*, 110*d*, 110*e*, and 110*f* is configured to rotate on the corresponding rotation axis. The driving of the actuators (not illustrated) is controlled, for example, by a processor functioning as the control unit (explained later) or an external medical controlling apparatus (not illustrated).

Each of the joint parts 110*a*, 110*b*, 110*c*, 110*d*, 110*e*, and 110*f* may be provided with an angle sensor (not illustrated) capable of detecting the rotation angle on the corresponding one of the six rotation axes. Examples of the angle sensor include an arbitrary sensor such as a rotary encoder or an angular velocity sensor capable of obtaining the rotation angle on the corresponding one of the six rotation axes.

As a result of each of the joint parts 110*a*, 110*b*, 110*c*, 110*d*, 110*e*, and 110*f* rotating on the corresponding rotation axis by being driven by the actuator (not illustrated), various operations of the arm 104 are realized, such as the arm 104 being extended or contracted (folded), for example.

The joint part 110*a* has a substantially circular columnar shape. A distal end part (a lower end part in FIG. 1) of the joint part 110*a* supports the imaging device 106 (an upper end part of the imaging device 106 in FIG. 1) so as to be rotatable on the rotation axis (the first axis O1) extending parallel to the central axis of the imaging device 106. In this situation, the medical observation apparatus 100 is configured so that the first axis O1 coincides with the optical axis of the imaging device 106. In other words, as a result of rotating the imaging device 106 on the first axis O1 illustrated in FIG. 1, a medical captured image taken by the imaging device 106 is an image of which the field of vision can be changed so as to rotate.

The link 112a is a substantially bar-like member and is configured to support the joint part 110a in a fixed manner. For example, the link 112a is arranged to extend in a direction orthogonal to the first axis O1 and is connected to the joint part 110b.

The joint part 110b has a substantially circular columnar shape and is configured to support the link 112a so as to be rotatable on the rotation axis (the second axis O2) orthogonal to the first axis O1. Further, to the joint part 110b, the link 112b is connected in a fixed manner.

The link 112b is a substantially bar-like member and arranged to extend in a direction orthogonal to the second axis O2. Further, to the link 112b, the joint part 110b and the joint part 110c are each connected.

The joint part 110c has a substantially circular columnar shape and is configured to support the link 112b so as to be rotatable on the rotation axis (the third axis O3) orthogonal to the first axis O1 and to the second axis O2. Further, to the joint part 110c, one end of the link 112c is connected in a fixed manner.

In this situation, as a result of the distal end side (the side on which the imaging device 106 is provided) of the arm 104 rotating on the second axis O2 and the third axis O3, it is possible to move the imaging device 106 so as to change the position of the imaging device 106 on a horizontal plane. In other words, with the medical observation apparatus 100, as a result of controlling the rotations on the second axis O2 and the third axis O3, it is possible to move the field of vision of the medical captured image on a plane.

The link 112c is a member of which one end has a substantially circular columnar shape, while the other end has a substantially-bar like shape. To the one end side of the link 112c, the joint part 110c is connected in a fixed manner, so that the central axis of the joint part 110c coincides with the central axis of the substantially circular columnar shape. Further, to the other end side of the link 112c, the joint part 110d is connected.

The joint part 110d has a substantially circular columnar shape and is configured to support the link 112c so as to be rotatable on the rotation axis (the fourth axis O4) orthogonal to the third axis O3. To the joint part 110d, the link 112d is connected in a fixed manner.

The link 112d is a substantially bar-like member and arranged to extend orthogonally to the fourth axis O4. One end of the link 112d is connected to the joint part 110d in a fixed manner so as to abut against the lateral face of the substantially circular columnar shape of the joint part 110d. Further, to the other end (the end opposite from the side to which the joint part 110d is connected) of the link 112d, the joint part 110e is connected.

The joint part 110e has a substantially circular columnar shape and is configured to support one end of the link 112d so as to be rotatable on the rotation axis (the fifth axis O5) extending parallel to the fourth axis O4. Further, to the joint part 110e, one end of the link 112e is connected in a fixed manner.

In this situation, the fourth axis O4 and the fifth axis O5 are rotation axes on which the imaging device 106 can move in vertical directions. As a result of the distal end side (the side on which the imaging device 106 is provided) of the arm 104 rotating on the fourth axis O4 and the fifth axis O5, the position of the imaging device 106 in terms of the vertical directions changes. Accordingly, as a result of the distal end side (the side on which the imaging device 106 is provided) of the arm 104 rotating on the fourth axis O4 and the fifth axis O5, it is possible to change the distance between the imaging device 106 and an observed object such as a surgery site of a patient.

The link 112e is a member configured by combining together: a substantially L-shaped first member of which one segment extends in a vertical direction, while the other segment extends in a horizontal direction; and a bar-like second member that extends vertically downward from the section of the first member extending in the horizontal direction. Of the link 112e, to the section of the first member extending in the vertical direction, the joint part 110e is connected in a fixed manner. Further, to the second member of the link 112e, the joint part 110f is connected.

The joint part 110f has a substantially circular columnar shape and is configured to support the link 112e so as to be rotatable on the rotation axis (the six axis O6) extending parallel to the vertical directions.

Further, to the joint part 110f, the link 112f is connected in a fixed manner.

The link 112f is a substantially bar-like member and arranged to extend in a vertical direction. To one end of the link 112f, the joint part 110f is connected. Further, the other end (the end opposite from the side to which the joint part 110f is connected) of the link 112f is connected to the base 102 in a fixed manner.

In the medical observation apparatus 100, because the arm 104 has the configuration described above, the six degrees of freedom are realized in relation to the moving of the imaging device 106.

Possible configurations of the arm 104 are not limited to the example described above.

For example, each of the joint parts 110a, 110b, 110c, 110d, 110e, and 110f of the arm 104 may be provided with a brake configured to regulate the rotation of the corresponding one of the joint parts 110a, 110b, 110c, 110d, 110e, and 110f. Examples of the brake according to the present embodiment include brakes using an arbitrary scheme such as a brake driven mechanically or an electromagnetic brake driven electrically.

The driving of the brake is controlled by, for example, a processor that functions as the control unit (explained later) or an external medical controlling apparatus (not illustrated). As a result of the driving of the brake being controlled, an operation mode of the arm 104 is set in the medical observation apparatus 100. Examples of the operation mode of the arm 104 include a fixed mode and a free mode.

In this situation, the fixed mode according to the present embodiment is an operation mode in which, for example, as a result of the rotations on the rotation axes provided in the arm 104 being regulated by the brakes, the position and the posture of the imaging device 106 are fixed. While the arm 104 is in the fixed mode, the operation state of the medical observation apparatus 100 is in a fixed state in which the position and the posture of the imaging device 106 are fixed.

In contrast, the free mode according to the present embodiment is an operation mode in which, as a result of the brakes being released, the rotation axes provided in the arm 104 are freely rotatable. For example, in the free mode, the position and the posture of the imaging device 106 can be adjusted by direct operations performed by the practitioner. In this situation, the direct operations according to the present embodiment denote operations in which, for example, the practitioner grips the imaging device 106 with his/her hand(s) so as to directly move the imaging device 106.

[1-1-2-3] The imaging device 106

The imaging device 106 is supported by the arm 104 and is configured to image an observed object such as a surgery site of a patient, for example. Imaging processes by the imaging device 106 are controlled, for example, by a processor that functions as the control unit (explained later) or an external medical controlling apparatus (not illustrated).

The imaging device 106 has a configuration corresponding to that of an electronically imaging microscope, for example.

Figure 3:
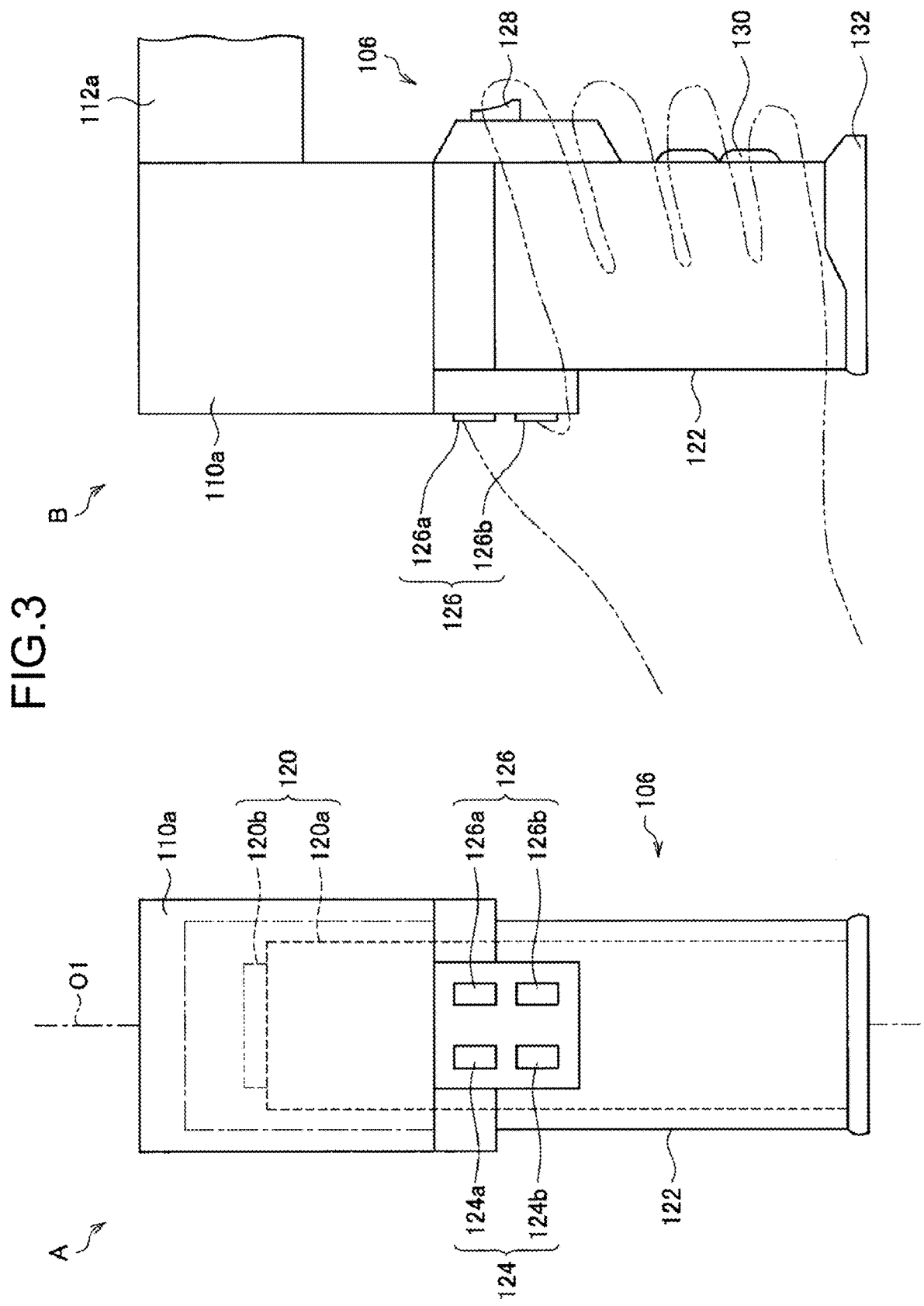
FIG. 3 is an explanatory drawing for explaining an example of a configuration of an imaging device included in a medical observation apparatus according to the present embodiment.

FIG. 3 is an explanatory drawing for explaining an example of a configuration of the imaging device 106 included in the medical observation apparatus 100 according to the present embodiment.

For example, the imaging device 106 includes an imaging member 120 and a cylindrical member 122 having a substantially circular cylindrical shape. The imaging member 120 is provided in the cylindrical member 122.

On the opening plane at the lower end (the end on the bottom side in FIG. 3) of the cylindrical member 122, for example, a cover glass (not illustrated) for protecting the imaging member 120 is provided.

Further, for example, a light source (not illustrated) is provided inside the cylindrical member 122 so that, at the time of imaging, illumination light is radiated from the light source onto the imaged subject through the cover glass. Reflection light (observation light) from the imaged subject onto which the illumination light was radiated becomes incident to the imaging member 120 via the cover glass (not illustrated). As a result, an image signal representing the imaged subject (an image signal representing a medical captured image) is acquired by the imaging member 120.

A configuration used in any of various types of publicly-known electronically imaging microscope units may be applied to the imaging member 120.

In one example, the imaging member 120 may be configured with: an optical system 120a; and an image sensor 120b including an imaging element configured to pick up an image of the observed object by using light that has passed through the optical system 120a. The optical system 120a is configured with optical elements such as one or more lenses (e.g., objective lenses, zoom lenses, focus lenses) and a mirror. Examples of the image sensor 120b include an image sensor using a plurality of imaging elements such as Complementary Metal Oxide Semiconductor (CMOS) elements or Charge Coupled Devices (CODs).

For example, by having two or more imaging devices each configured with the optical system 120a and the image sensor 120b, the imaging member 120 is configured to function as a so-called stereo camera. In configurations of the imaging devices 106 functioning as a stereo camera, the optical system may be a Galilean optical system or a Greenough optical system.

The following will describe an example in which the medical observation apparatus 100 according to the present embodiment which may be the medical observation apparatus 100 structuring the medical observation system according to the second example (explained later) includes a plurality of imaging devices that function as a stereo camera, so that a plurality of medical captured images including a medical captured image for the right eye (hereinafter, simply "right-eye medical captured image") and a medical captured image for the left eye (hereinafter, simply "left-eye medical captured image") are acquired from imaging processes each of which is performed by a different one of the plurality of imaging devices.

The imaging device structuring the imaging member 120 has installed therein one or more functions that are generally provided in an electronically imaging microscope unit, such as a zoom function (one or both of an optical zoom function and an electronic zoom function) and an Auto Focus (AF) function.

Further, the imaging member 120 may be configured to be able to perform a so-called high-resolution imaging process such as 4K or 8K, for example. When the imaging member 120 is configured to be able to perform the high-resolution imaging process, it is possible to display images on the display device 200 having a large display screen (e.g., 50 inch or larger) while ensuring a predetermined resolution (e.g., full HD image quality). The visibility is thus enhanced for the practitioner who views the display screen. Further, when the imaging member 120 is configured to be able to perform the high-resolution imaging process, it is possible to ensure a predetermined resolution, even when a captured image is displayed on the display screen of the display device 200 while being enlarged by the electronic zoom function. Further, when the predetermined resolution is ensured by using the electronic zoom function, it is possible to suppress capabilities of the optical zoom function of the imaging device 106. Accordingly, it is possible to keep the optical system of the imaging device 106 simpler and to keep the imaging device 106 more compact.

For example, the imaging device 106 is provided with various types of operation devices for controlling operations of the imaging device 106. In the example in FIG. 3, the imaging device 106 is provided with a zoom switch 124, a focus switch 126, and an operation mode changing switch 128. Needless to say, the positions and the shapes of the zoom switch 124, the focus switch 126, and the operation mode changing switch 128 are not limited to those in the example illustrated in FIG. 3.

The zoom switch 124 and the focus switch 126 are examples of operation devices for adjusting image taking conditions of the imaging device 106.

The zoom switch 124 is, for example, configured with a zoom-in switch 124a used for increasing a zoom ratio (an enlargement ratio) and a zoom-out switch 124b used for reducing the zoom ratio. As a result of an operation performed on the zoom switch 124, the zoom ratio is adjusted so that the zoom is adjusted.

The focus switch 126 is, for example, configured with a distant-view focus switch 126a used for increasing a focal distance to the observed object (the imaged subject) and a close-view focus switch 126b used for shortening the focal distance to the observed object. As a result of an operation performed on the focus switch 126, the focal distance is adjusted, so that the focus is adjusted.

The operation mode changing switch 128 is an example of an operation device for changing the operation mode of the arm 104 of the imaging device 106. As a result of an operation performed on the operation mode changing switch 128, the operation mode of the arm 104 is changed. Examples of the operation mode of the arm 104 include the fixed mode and the free mode, as described above.

Examples of the operation performed on the operation mode changing switch 128 include an operation to press the operation mode changing switch 128. For example, while the practitioner is pressing the operation mode changing switch 128, the operation mode of the arm 104 is the free mode. In contrast, while the practitioner is not pressing the operation mode changing switch 128, the operation mode of the arm 104 is the fixed mode.

Further, the imaging device 106 is provided with, for example, a slip prevention member 130 and a projection member 132, to enhance operability and convenience of operations performed by the operator who operates various types of operation devices.

The slip prevention member 130 is a member provided to prevent an operation body (e.g., the operator's hand) from slipping, when the operator operates the cylindrical member 122 by using the operation body, for example. The slip prevention member 130 is, for example, formed by using a material having a large friction coefficient and has a structure that slips less easily such as an uneven surface.

The projection member 132 is a member provided to prevent the operation body from blocking the field of vision of the optical system 120a while the operator is operating the cylindrical member 122 by using the operation body such as his/her hand and to prevent the cover glass (not illustrated) from being smudged as a result of the operation body coming into contact with the cover glass while the operator is performing an operation by using the operation body.

Needless to say, the positions and the shapes of the slip prevention member 130 and the projection member 132 are not limited to those in the example illustrated in FIG. 3. Further, one or both of the slip prevention member 130 and the projection member 132 may not be provided for the imaging device 106.

On the image signal (image signal data) generated from the imaging process performed by the imaging device 106, an image processing process is performed, for example, by a processor that functions as the control unit (explained later). Examples of the image processing process according to the present embodiment include one or more processes selected from among various types of processes such as a gamma correction, white balance adjustments, image enlargement and/or reduction related to the electronic zoom function, and inter-pixel corrections.

When the medical observation system according to the present embodiment includes a medical controlling apparatus (not illustrated) configured to control various types of operations of the medical observation apparatus 100, the image processing process according to the present embodiment may be performed by the medical controlling apparatus (not illustrated).

For example, the medical observation apparatus 100 is configured to transmit a display control signal and the image signal on which the image processing process has been performed as described above, to the display device 200.

When the display control signal and the image signal have been transmitted to the display device 200, a display screen of the display device 200 displays a medical captured image taken of the observed object (e.g., a captured image taken of the surgery site), while being enlarged or reduced to a desired ratio by one or both of the optical zoom function and the electronic zoom function.

The medical observation apparatus 100 illustrated in FIG. 1 has, for example, the hardware configuration described with reference to FIGS. 1 and 3.

Possible hardware configurations of the medical observation apparatus according to the present embodiment are not limited to the configuration described with reference to FIGS. 1 and 3.

For example, the medical observation apparatus according to the present embodiment does not necessarily have to include the base 102 and may be configured so that the arm 104 is directly attached to the ceiling or a wall surface of the operating room or the like. For example, when the arm 104 is attached to the ceiling, the medical observation apparatus according to the present embodiment is configured so that the arm 104 is hung from the ceiling.

Further, although FIG. 1 illustrates the example in which the arm 104 is realized with the six degrees of freedom in relation to the driving of the imaging device 106, possible configurations of the arm 104 are not limited to the configuration in which there are six degrees of freedom related to the driving of the imaging device 106. For example, it is sufficient when the arm 104 is configured so as to be able to move the imaging device 106, as appropriate, in accordance with purposes of use. It is acceptable to set, as appropriate, the quantities and the positional arrangements of the joint parts and the links, as well as the directions of the drive axes of the joint parts so that the arm 104 has a desired degree of freedom.

Further, although FIGS. 1 and 3 illustrate the example in which the imaging device 106 is provided with the various types of operation devices used for controlling the operations of the imaging device 106, the imaging device 106 does not necessarily have to be provided with a part or all of the operation devices illustrated in FIGS. 1 and 3. In one example, the various types of operation devices used for controlling the operations of the imaging device 106 may be provided in other sections of the medical observation apparatus according to the present embodiment besides the imaging device 106. In another example, the various types of operation devices used for controlling the operations of the imaging device 106 may be external operation devices such as the foot switch FS, a remote controller, and the like.

Further, the imaging device 106 may be configured to be able to switch between a plurality of observation modes. Examples of the observation modes according to the present embodiment include an observation mode in which imaging is performed with natural light, an observation mode in which imaging is performed with special light, and an observation mode in which imaging is performed by using an image emphasis observation technique such as Narrow Band Imaging (NBI). For example, the special light according to the present embodiment is, as described above, light in a specific wavelength band such as light in a near-infrared wavelength band or light in a fluorescence wavelength band for fluorescence observation using 5-ALA.

Examples of the configuration of the imaging device 106 to be able to switch between the plurality of observation modes include "a configuration including: a filter configured to pass the light in a specific wavelength band and to not pass the light in the other wavelength bands; and a moving mechanism configured to selectively arrange the filter on an optical path". Examples of the specific wavelength band passed by the filter according to the present embodiment include: a near-infrared wavelength band (e.g., a wavelength band approximately from 0.7 [micrometers] to 2.5 [micrometers]); a fluorescence wavelength band for fluorescence observation using 5-ALA (e.g., a wavelength band approximately from 0.6 [micrometers] to 0.65 [micrometers]); and a fluorescence wavelength band of Indocyanine Green (ICG) (e.g., a wavelength band approximately from 0.82 [micrometers] to 0.85 [micrometers]).

The imaging device 106 may be provided with a plurality of filters that pass mutually-different wavelength bands. Further, in the example above, the imaging process is performed by using the light in the specific wavelength band, while arranging the filter on the optical path; however, needless to say, possible configurations of the imaging device 106 for performing the imaging process by using the light in a specific wavelength band are not limited to the example described above.

In the following sections, an imaging process in the observation mode in which an imaging device such as the imaging device 106 included in the medical observation apparatus 100 according to the present embodiment performs imaging while using special light will be referred to as a "special light observation".

[1-2] A medical observation system according to a second example

The medical observation system 1000 according to the present embodiment is not limited to the configuration in the first example illustrated in FIG. 1. Next, as another example of the medical observation system 1000, an example of a configuration of the medical observation system 1000 having the medical observation apparatus 100 functioning as an endoscope apparatus will be explained.

Figure 4:
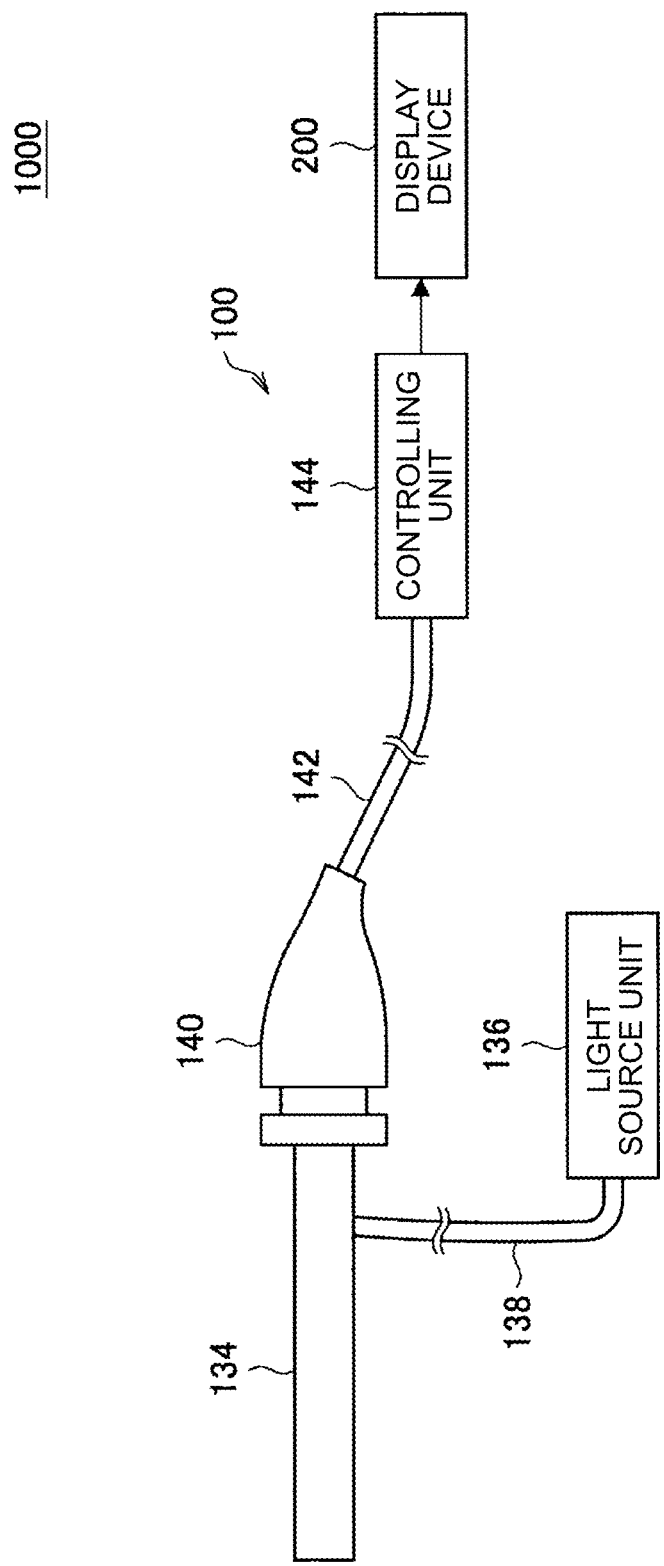
FIG. 4 is an explanatory drawing illustrating a second example of the configuration of the medical observation system according to the present embodiment.

FIG. 4 is an explanatory drawing illustrating a second example of the configuration of the medical observation system 1000 according to the present embodiment. The medical observation system 1000 illustrated in FIG. 4 includes, for example, the medical observation apparatus 100 and the display device 200. For example, when the medical observation apparatus 100 illustrated in FIG. 4 is used for surgery, the practitioner observes a surgery site while viewing a medical captured image taken by the medical observation apparatus 100 and displayed on a display screen of the display device 200, so as to perform, on the surgery site, various types of procedures such as a manipulation corresponding to a surgery scheme.

The medical observation system according to the second example is not limited to the example illustrated in FIG. 4.

For example, similarly to the medical observation system according to the first example, the medical observation system according to the second example also may further include a medical controlling apparatus (not illustrated) configured to control various types of operations of the medical observation apparatus 100.

Further, similarly to the medical observation system according to the first example, the medical observation system according to the second example may also be configured so as to include two or more medical observation apparatuses 100 and/or two or more display devices 200.

The following will describe, each of the apparatuses structuring the medical observation system 1000 according to the second example illustrated in FIG. 4.

[1-2-1] The display device 200

The display device 200 is a display means in the medical observation system 1000 according to the second example and corresponds to a display device external to the medical observation apparatus 100. The display device 200 structuring the medical observation system 1000 according to the second example is the same as the display device 200 structuring the medical observation system 1000 according to the first example.

[1-2-2] The medical observation apparatus 100

The medical observation apparatus 100 illustrated in FIG. 4 includes, for example, an insertion member 134, a light source unit 136, a light guide 138, a camera head 140, a cable 142, and a controlling unit 144. For example, the medical observation apparatus 100 is driven with electric power supplied from an internal power source such as a battery included in the medical observation apparatus 100 or electric power supplied from an external power source connected thereto.

The insertion member 134 has an elongated shape and includes, on the inside thereof, an optical system configured to converge incident light. The front end of the insertion member 134 is, for example, inserted in a body cavity of a patient. The rear end of the insertion member 134 is detachably connected to the front end of the camera head 140.

Further, the insertion member 134 is connected to the light source unit 136 via the light guide 138 and is configured to receive the light supplied from the light source unit 136.

For example, the insertion member 134 may be formed by using a material having no flexibility or may be formed by using a material having flexibility. Depending on the material forming the insertion member 134, the medical observation apparatus 100 may be called a rigid endoscope or a flexible endoscope.

The light source unit 136 is connected to the insertion member 134 via the light guide 138. The light source unit 136 is configured to supply the light to the insertion member 134 via the light guide 138.

For example, the light source unit 136 includes a plurality of light sources configured to emit light beams having mutually-different wavelengths. Examples of the plurality of light sources included in the light source unit 136 include a light source configured to emit red light, a light source configured to emit green light, and a light source configured to emit blue light. For example, the light source configured to emit the red light may be one or more red light emitting diodes. The light source configured to emit the green light may be one or more green light emitting diodes. The light source configured to emit the blue light may be one or more blue light emitting diodes. Needless to say, the plurality of light sources included in the light source unit 136 are not limited to the examples described above. For example, the light source unit 136 may include the plurality of light sources as a single chip or may include the plurality of light sources as multiple chips.

The light source unit 136 is connected to the controlling unit 144 in a wired or wireless manner. The light emission of the light source unit 136 is controlled by the controlling unit 144.

The light supplied to the insertion member 134 is ejected from the front end of the insertion member 134 and radiated onto an observed object such as a tissue in the body cavity of the patient. Further, reflection light from the observed object is converged by the optical system provided in the insertion member 134.

The camera head 140 has a function of imaging the observed object. The camera head 140 is connected to the controlling unit 144 via the cable 142 serving as a signal transfer member.

The camera head 140 includes an image sensor and is configured to image the observed object by performing a photoelectric conversion on the reflection light from the observed object converged by the insertion member 134 and to output an image signal (a signal representing the medical captured image) acquired in the imaging process to the controlling unit 144 via the cable 142. The image sensor included in the camera head 140 may be, for example, an image sensor using a plurality of imaging elements such as CMOS elements or CCDs.

In the medical observation apparatus 100 functioning as an endoscope apparatus, for example, the insertion member 134, the light source unit 136, and the camera head 140 play the role of an "imaging device inserted into the inside of the body of a patient, so as to image the inside of the body".

The medical observation apparatus 100 functioning as an endoscope apparatus may be configured, for example, so as to include a plurality of imaging devices that function as a stereo camera. In configurations of the imaging devices that function as a stereo camera, the optical system may be a Galilean optical system or a Greenough optical system, similarly to the medical observation apparatus 100 structuring the medical observation system according to the first example.

Further, the imaging device included in the medical observation apparatus 100 functioning as an endoscope apparatus may be configured so as to be able to switch between a plurality of observation modes such as an observation mode in which imaging is performed with natural light, an observation mode in which imaging is performed with special light, and/or the like.

The controlling unit 144 is configured to control the imaging device. More specifically, the controlling unit 144 is configured to control the light source unit 136 and the camera head 140.

Further, the controlling unit 144 includes a communication device (not illustrated) and is configured to transmit the image signal output from the camera head 140 to the display device 200 through arbitrary wireless communication or arbitrary wired communication. The controlling unit 144 may transmit the image signal and a display control signal to the display device 200.

Examples of the communication device (not illustrated) included in the controlling unit 144 include an IEEE 802.15.1 port with a transmission/reception circuit (wireless communication), an IEEE 802.11 port with a transmission/reception circuit (wireless communication), a communication antenna with an RF circuit (wireless communication), an optical communication device (wired or wireless communication), and a LAN terminal with a transmission/reception circuit (wired communication). The communication device (not illustrated) may be configured to be able to communicate with one or more external devices by using a plurality of communication schemes.

Further, the controlling unit 144 may be configured to perform a predetermined process on the image signal output from the camera head 140 and to transmit the image signal on which the predetermined process has been performed to the display device 200. Examples of the predetermined process performed on the image signal include white balance adjustments, image enlargement and/or reduction related to the electronic zoom function, and inter-pixel corrections.

Further, the controlling unit 144 may be configured to store therein a medical captured image based on the image signal.

Examples of the controlling unit 144 include a Camera Control Unit (CCU).

The medical observation apparatus 100 functioning as an endoscope apparatus has, for example, the hardware configuration described with reference to FIG. 4. For instance, in the medical observation apparatus 100 functioning as an endoscope apparatus, the insertion member 134, the light source unit 136, and the camera head 140 play the role of an imaging device, while the controlling unit 144 is configured to control imaging processes performed by the imaging device.

[1-3] A functional configuration of the medical observation apparatus 100

Figure 5:
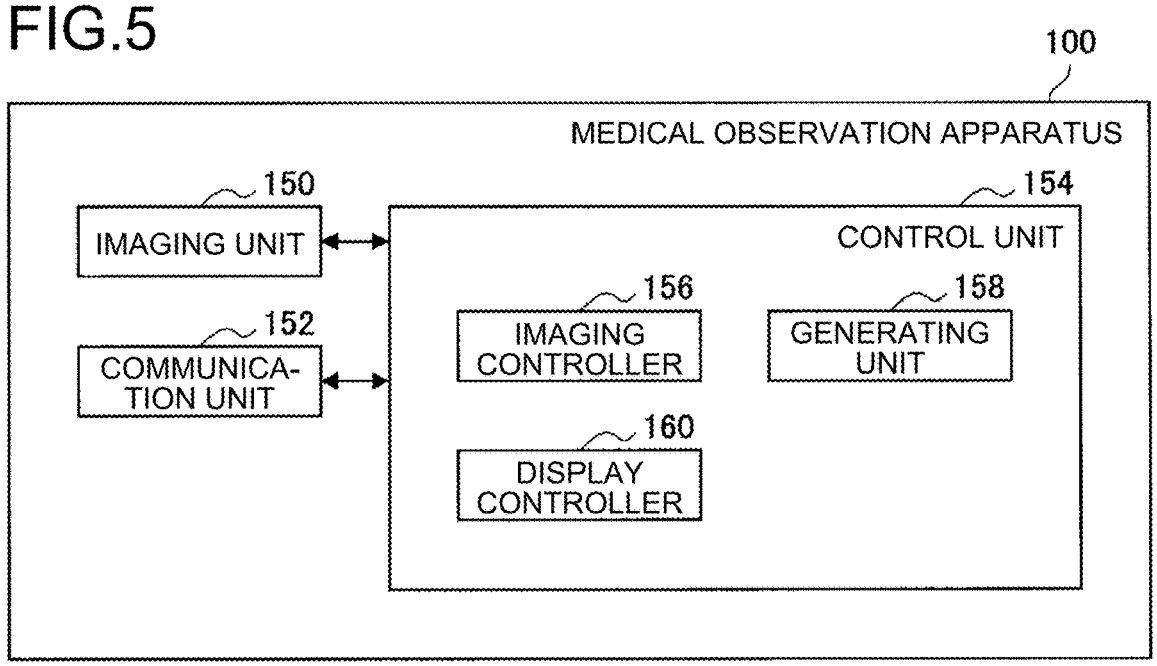
FIG. 5 is a functional block diagram illustrating an example of a configuration of the medical observation apparatus according to the present embodiment.

Next, the medical observation apparatus 100 illustrated in FIGS. 1 and 4 will be explained with reference to a functional block. FIG. 5 is a functional block diagram illustrating an example of a configuration of the medical observation apparatus 100 according to the present embodiment.

The medical observation apparatus 100 includes, for example, an imaging unit 150, a communication unit 152, and a control unit 154.

The imaging unit 150 is configured to image an observed object. For example, the imaging unit 150 is configured with the "imaging device 106" (in the example of the medical observation apparatus 100 illustrated in FIG. 1) or with "the insertion member 134, the light source unit 136, and the camera head 140" (in the example of the medical observation apparatus 100 illustrated in FIG. 4). Imaging processes performed by the imaging unit 150 are controlled by the control unit 154, for example.

The communication unit 152 is a communication means included in the medical observation apparatus 100 and plays the role of communicating with external devices such as the display device 200 in a wireless or wired manner. For example, the communication unit 152 is configured with the communication device (not illustrated) described above. The communication performed by the communication unit 152 is controlled by the control unit 154, for example.

For example, the control unit 154 is configured with the processor (not illustrated) described above and plays the role of controlling the entirety of the medical observation apparatus 100. Further, the control unit 154 plays the role of taking initiative in processes related to the display controlling method (explained later). The processes related to the display controlling method performed by the control unit 154 may be performed by a plurality of processing circuits (e.g., a plurality of processors) in a distributed manner.

More specifically, the control unit 154 includes, for example, an imaging controller 156, a generating unit 158, and a display controller 160.

The imaging controller 156 is configured to control the one or more imaging devices structuring the imaging unit 150. Examples of the control exercised over the imaging device include controlling one or more functions that are generally provided in electronically imaging microscope units, such as controlling an AF function including at least zoom functions (an optical zoom function and an electronic zoom function).

The generating unit 158 plays the role of performing a generating process (explained later), which is a part of the processes related to the display controlling method according to the present embodiment. For example, the generating unit 158 is configured to generate a three-dimensional model of an observed object, based on the right-eye medical captured image and the left-eye medical captured image. An example of the generating process related to the display controlling method according to the present embodiment will be explained later.

The display controller 160 plays the role of performing a display controlling process (explained later), which is a part of the processes related to the display controlling method according to the present embodiment and is configured to, for example, control the display on a display screen such as a display screen of the display device 200.

The display controller 160 is configured, for example, to cause a display screen to display the three-dimensional model generated by the generating unit 158. For example, when the imaging device structuring the imaging unit 150 has performed a special light observation and acquired a special light observation image for the right eye (hereinafter, simply "right-eye special light observation image") and a special light observation image for the left eye (hereinafter, simply "left-eye special light observation image"), the display controller 160 causes a display screen to display, for example, a result of combining the three-dimensional model with the right-eye special light observation image and the left-eye special light observation image. In another example, when biological information has been acquired from an external biological information acquiring apparatus (either directly or via another apparatus), the display controller 160 causes a display screen to display a result of combining the three-dimensional model with the acquired biological information. "An example of the display controlling process related to the display controlling method according to the present embodiment", "an example of the display combining the three-dimensional model with the right-eye special light observation image and the left-eye special light observation image", and "an example of the display combining the three-dimensional model with the biological information" will be explained later.

Possible examples of the control over the display on the display screen exercised by the display controller 160 are not limited to the example described above.

For example, the display controller 160 is capable of controlling the display of a medical captured image on a display screen. For example, the display controller 160 is configured to exercise control (3D display control) in which the right-eye medical captured image and the left-eye medical captured image are each displayed on a display screen. Alternatively, the display controller 160 is also capable of controlling two-dimensional (2D) display, by causing one of the right-eye and the left-eye medical captured images to be displayed. The following will describe an example in which the display controller 160 causes a display screen to display the right-eye medical captured image and the left-eye medical captured image.

Further, the display controller 160 may also control the display of various images such as images related to a UI being displayed on a display screen.

For example, the display controller 160 is configured to control the display of the display device 200, by transferring the display control signal and the image signal to the communication device (not illustrated) structuring the communication unit 152 and causing the display control signal and the image signal to be transmitted to the display device 200. In this situation, the control over the communication performed by the communication unit 152 may be exercised by a communication controller (not illustrated) structuring the control unit 154.

Further, the display controller 160 may record data corresponding to the image signal onto a recording medium (not illustrated) functioning as a storage unit (not illustrated) or onto an arbitrary recording medium such as an external recording medium. The data corresponding to the image signal and being recorded on the recording medium may be "data combining a three-dimensional model with a right-eye special light observation image and a left-eye special light observation image" or "data combining a three-dimensional model with biological information" explained later.

The three-dimensional model and the data to be combined with the three-dimensional model may be recorded while being kept in correspondence with each other by using an arbitrary method. Further, regardless of whether the data is to be combined with a three-dimensional model, the display controller 160 may record other data besides the three-dimensional model, such as data indicating measuring positions of the biological information acquiring apparatus, so as to be kept in correspondence with the three-dimensional model.

For example, by having the generating unit 158 and the display controller 160, for example, the control unit 154 plays the role of taking initiative in the processes related to the display controlling method according to the present embodiment. Further, by having the imaging controller 156 and the display controller 160, for example, the control unit 154 plays the role of controlling the entirety of the medical observation apparatus 100.

Possible functional configurations of the control unit 154 are not limited to the example illustrated in FIG. 5.

For example, the control unit 154 may have an arbitrary configuration corresponding to divisions of functions of the medical observation apparatus 100, such as a configuration corresponding to divisions of the processes related to the display controlling method according to the present embodiment.

In one example, when the medical observation apparatus 100 has the configuration illustrated in FIG. 1, the control unit 154 may further include an arm controller (not illustrated) configured to control driving of the arm 104. Examples of the control over the driving of the arm 104 include "applying a control signal for controlling the driving to each of the actuators (not illustrated) respectively corresponding to the joint parts 110*a*, 110*b*, 110*c*, 110*d*, 110*e*, and 110*f*".

By using the functional configuration illustrated in FIG. 5, for example, the medical observation apparatus 100 is configured to perform the processes related to the display controlling method according to the present embodiment described later.

Possible functional configurations of the medical observation apparatus according to the present embodiment are not limited to the configuration illustrated in FIG. 5.

For example, the medical observation apparatus according to the present example may include a part or all of the imaging controller 156, the generating unit 158, and the display controller 160 illustrated in FIG. 5 separately from the control unit 154 (so as to be, for example, realized with one or more different processing circuits).

Further, possible functional configurations of the medical observation apparatus according to the present embodiment capable of executing the processes related to the display controlling method according to the present embodiment are not limited to the configuration illustrated in FIG. 5. For example, the medical observation apparatus according to the present embodiment may have a functional configuration corresponding to divisions of the processes related to the display controlling method according to the present embodiment.

Further, when the medical observation apparatus according to the present embodiment has the configuration illustrated in FIG. 1, the medical observation apparatus according to the present embodiment includes an arm unit (not illustrated) configured with the arm 104. The arm 104 structuring the arm unit (not illustrated) is configured to support the imaging device 106 structuring the imaging unit 150.

Further, for example, when communicating with an external device via an external communication device having functions and a configuration that are the same as or similar to those of the communication unit 152, the medical observation apparatus according to the present embodiment does not necessarily have to include the communication unit 152.

Further, when the medical observation system according to the present embodiment includes a medical controlling apparatus (not illustrated), while the medical observation apparatus according to the present embodiment is configured to be controlled by the medical controlling apparatus (not illustrated), the medical observation apparatus according to the present embodiment does not necessarily have to include the control unit 154.

In this situation, for example, by including a control unit having functions and a configuration that are the same as or similar to those of the control unit 154, the medical controlling apparatus (not illustrated) is configured to perform the processes related to the display controlling method (explained later) according to the present embodiment and is also configured to control operations of constituent elements of the medical observation apparatus according to the present embodiment, such as the imaging unit 150. The medical controlling apparatus (not illustrated) is configured to control the operations of the constituent elements of the medical observation apparatus according to the present embodiment, by communicating with the medical observation apparatus according to the present embodiment via a communication device included therein or via an external communication device connected thereto.

Further, when the medical observation system according to the present embodiment includes a medical controlling apparatus (not illustrated), while the medical observation apparatus according to the present embodiment is configured to be controlled by the medical controlling apparatus (not illustrated), the medical observation apparatus according to the present embodiment may be configured so as not to include a part of the functions of the control unit 154.

[2] A display controlling method according to the present embodiment

Next, a display controlling method according to the present embodiment will be explained. The following will describe an example in which processes related to the display controlling method according to the present embodiment are performed by the medical observation apparatus 100 (more specifically, for example, the generating unit 158 and the display controller 160 included in the control unit 154 structuring the medical observation apparatus 100). As explained above, in the medical observation system according to the present embodiment, the processes related to the display controlling method according to the present embodiment may be performed by the display device 200 or a medical controlling apparatus (not illustrated).

As explained above, even when a special light observation is performed, when the acquired special light observation image has much dark noise due to insufficient levels of brightness and/or contrast, there is a possibility that medical providers may be unable to easily identify the position of a blood vessel or a tumor in the observed object.

Further, as explained above, when a biological information acquiring apparatus is used in actual medical settings, medical providers such as practitioners and assistants perform medical procedures such as manipulations by putting together, in their heads, the state of the observed object represented by a medical captured image with the content of the biological information. For this reason, medical providers may feel burdened in some situations.

To cope with those situations, the medical observation apparatus 100 is configured to generate a three-dimensional model of an observed object and to cause a display screen to display a result of combining the three-dimensional model with a right-eye special light observation image and a left-eye special light observation image or to cause a display screen to display a result of combining the three-dimensional model with biological information acquired by an external biological information acquiring apparatus. As described in the application examples of the display controlling method presented below, the three-dimensional model of the observed object indicates an anatomical structure of the observed object. In other words, it can be said that the biological information according to the present embodiment which can be combined with a three-dimensional model is information corresponding to the anatomical structure.

As a result of the medical observation apparatus 100 causing the result of combining the three-dimensional model with either the special light observation images or the biological information to be displayed, the display screen displays an image in which either the content based on the special light observation images or the content based on the biological information is integrated with the three-dimensional model.

In this situation, as a result of the content based on the special light observation images being integrated with the three-dimensional model, medical providers become able to identify the position of a blood vessel, a tumor, or the like in the observed object more easily than when viewing the special light observation images. Further, as a result of the content based on the biological information being integrated with the three-dimensional model, medical providers do not need to put together, in their heads, the state of the observed object represented by the medical captured images with the content of the biological information.

Accordingly, as a result of the processes related to the display controlling method according to the present embodiment being performed, it is possible to enhance the convenience of the medical providers.

More specifically, as the processes related to the display controlling method according to the present embodiment, the medical observation apparatus 100 performs, for example, a generating process described in section (1) below and a display controlling process described in section (2) below.

(1) A generating process

The medical observation apparatus 100 generates the three-dimensional model of the observed object based on the right-eye medical captured image and the left-eye medical captured image.

For example, the medical observation apparatus 100 obtains a "distance between the right-eye medical captured image and the left-eye medical captured image in each pair of corresponding positions thereof" and further generates the three-dimensional model from the obtained distances. Examples of the three-dimensional model generated by the medical observation apparatus 100 will be explained later.

The "distance between the right-eye medical captured image and the left-eye medical captured image in each pair of corresponding positions thereof" is obtained by performing the process described in section (a) and the process described in section (b) below. The processes in sections (a) and (b) may be performed by the medical observation apparatus 100 or may be performed by an apparatus (e.g., a medical controlling apparatus (not illustrated)) external to the medical observation apparatus 100. The following will describe an example in which the processes in sections (a) and (b) are performed by the medical observation apparatus 100.

(a) A correspondence keeping process

For example, the medical observation apparatus 100 brings the right-eye medical captured image and the left-eye medical captured image into correspondence with each other by extracting a feature part from each of the right-eye and the left-eye medical captured images and matching the extracted feature parts with each other.

The feature parts in the medical captured images are extracted, for example, by using an arbitrary technique capable of extracting feature parts from images, such as using one or both of an edge detected by an arbitrary edge detecting process and a result of an arbitrary perimeter examination process. Further, for example, the medical observation apparatus 100 brings the right-eye medical captured image and the left-eye medical captured image into correspondence with each other, by using an arbitrary technique, such as pattern matching, capable of identifying identical imaged subjects by comparing the extracted feature parts.

(b) A distance calculating process

The medical observation apparatus 100 calculates the distance between each pair of corresponding points that are brought into correspondence by performing the process in section (a) above (i.e., the correspondence keeping process).

For example, by performing the calculation presented in Mathematical Formula 1 below, the medical observation apparatus 100 calculates a distance z. In Mathematical Formula 1, "h" denotes the distance (i.e., the base line length) between the imaging device that images the right-eye medical captured image and the imaging device that images the left-eye medical captured image and is a known value. In Mathematical Formula 1 below, "f" denotes the focal distance between the imaging device that images the right-eye medical captured image and the imaging device that images the left-eye medical captured image and is a known value. In Mathematical Formula 1 below, "x" denotes the x coordinate of a corresponding point in the left-eye medical captured image. In Mathematical Formula 1 below, "x'" denotes the x coordinate of a corresponding point in the right-eye medical captured image.

$$z = h \cdot f / |x - x'| \quad \text{(Mathematical Formula 1)}$$

For example, by performing the processes in sections (a) and (b) above, it is possible to obtain the "distance between the right-eye medical captured image and the left-eye medical captured image in each pair of corresponding positions thereof". Needless to say, possible processes capable of obtaining the "distance between the right-eye medical captured image and the left-eye medical captured image in each pair of corresponding positions thereof" are not limited to the processes described in sections (a) and (b) above.

(2) A display controlling process

For example, the medical observation apparatus 100 either combines the three-dimensional model generated in the process in section (1) above (i.e., the generating process) with the right-eye special light observation image and the left-eye special light observation image, or combines the three-dimensional model with the biological information. Further, the medical observation apparatus 100 causes a display screen to display the combined result.

For example, when the imaging device structuring the imaging unit 150 has performed a special light observation and acquired the right-eye special light observation image and the left-eye special light observation image, the medical observation apparatus 100 combines the three-dimensional model with the right-eye special light observation image and the left-eye special light observation image. In another example, when biological information has been acquired from an external biological information acquiring apparatus (either directly or via another apparatus), the medical observation apparatus 100 combines the three-dimensional model with the biological information. "An example of display combining the three-dimensional model with the right-eye special light observation image and the left-eye special light observation image" and "an example of display combining the three-dimensional model with the biological information" will be explained later.

Possible display controlling processes related to the display controlling method according to the present embodiment are not limited to the example described above.

For example, the medical observation apparatus 100 may cause three-dimensional models generated at different points in time in a predetermined time period to be sequentially displayed in a time series. As a result of the three-dimensional models being sequentially displayed in the time series, the three-dimensional model also moves in accordance with moves of the observed object in the predetermined time period. Accordingly, as a result of the three-dimensional models being sequentially displayed in the time series, the viewer of the display screen is able to recognize, from the three-dimensional models, the moves of the observed object in the predetermined time period. Further, also when the three-dimensional models are sequentially displayed in the time series, an advantage effect is achieved where it is possible to enhance the convenience of medical providers, as a result of "the medical observation apparatus 100 combining each of the three-dimensional models sequentially displayed in the time series with either the special light observation images at the corresponding point in time or the biological information at the corresponding point in time".

In this situation, the three-dimensional models are generated from the "distance between the right-eye medical captured image and the left-eye medical captured image in each pair of corresponding positions thereof". Accordingly, generating a three-dimensional model at each of the different points in time during the predetermined time period corresponds to acquiring data indicating moves of the observed object expressed with numerical values.

Further, for example, as described above, the medical observation apparatus 100 may record the data corresponding to the image signal in an arbitrary recording medium such as a recording medium (not illustrated) that functions as a storage unit (not illustrated). Further, the medical observation apparatus 100 may record the three-dimensional model and other data besides the three-dimensional model onto an arbitrary recording medium so as to be kept in correspondence with each other.

As the processes related to the display controlling method according to the present embodiment, the medical observation apparatus 100 performs, for example, the process in section (1) (the generating process) and the process in section (2) (the display controlling process) described above. The process in section (1) (the generating process) and the process in section (2) (the display controlling process) described above are obtained by dividing the processes related to the display controlling method according to the present embodiment for the sake of convenience. In other words, possible methods for dividing the processes related to the display controlling method according to the present embodiment are not limited to having the process in section (1) (the generating process) and the process in section (2) (the display controlling process) described above.

[3] Application examples of the display controlling method according to the present embodiment Next, with application example of the display controlling method according to the present embodiment, an example of the processes related to the display controlling method according to the present embodiment will be explained. Needless to say, possible application examples of the display controlling method according to the present embodiment are not limited to the application examples described below.

[3-1] A first application example of the display controlling method according to the present embodiment: An example of the display combining a three-dimensional model with a right-eye special light observation image and a left-eye special light observation image The following will describe an example of the display combining the three-dimensional model with the right-eye special light observation image and the left-eye special light observation image.

Figure 6:
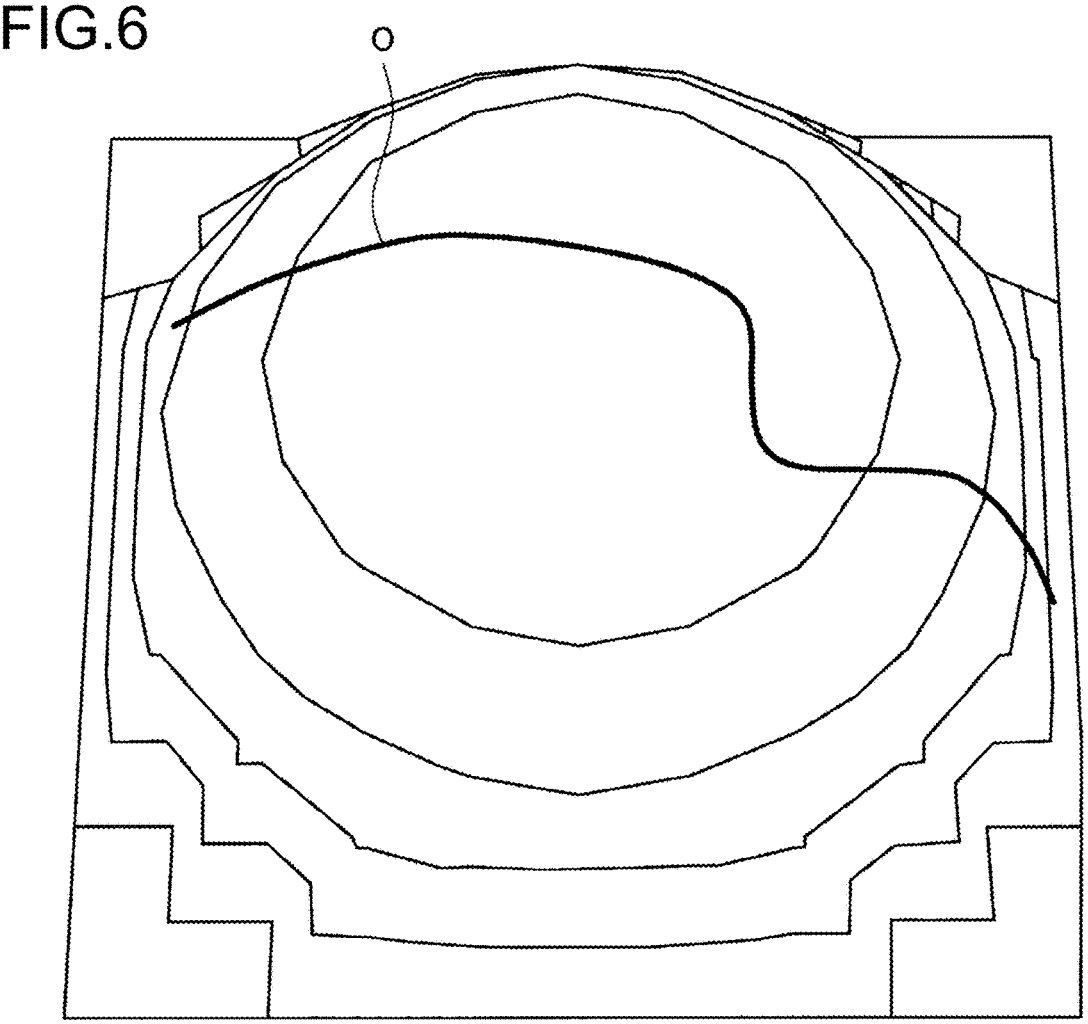
FIG. 6 is an explanatory drawing illustrating an example of a medical captured image according to the present embodiment.

FIG. 6 is an explanatory drawing illustrating an example of a medical captured image according to the present embodiment. The letter "0" in FIG. 6 indicates a blood vessel that is present in a surgery site (a lesion) of an observed object. Blood vessels present in observed objects are difficult to be visually recognized when the imaging is performed with natural light and are easy to be visually recognized when a special light observation is performed by using light in a near-infrared wavelength band.

For example, as illustrated in FIG. 6, the medical observation apparatus 100 generates a three-dimensional model of the observed object from a right-eye medical captured image and a left-eye medical captured image taken of the observed object.

When the three-dimensional model has been generated, the medical observation apparatus 100 combines the three-dimensional model with a right-eye special light observation image and a left-eye special light observation image.

For example, by performing the process in section (a) (i.e., the correspondence keeping process) and the process in section (b) (i.e., the distance calculating process) described above, the medical observation apparatus 100 calculates distances from the right-eye special light observation image and the left-eye special light observation image. Further, the medical observation apparatus 100 corrects the distances calculated from the right-eye special light observation image and the left-eye special light observation image, by using distances calculated from the right-eye medical captured image and the left-eye medical captured image. After that, based on the result of the correction, the medical observation apparatus 100 combines the three-dimensional model with the right-eye special light observation image and the left-eye special light observation image.

In this situation, the reason for correcting the distances calculated from the right-eye special light observation image and the left-eye special light observation image is that, for example, the acquired special light observation images may, in some situations, have much dark noise due to insufficient levels of brightness and/or contrast.

Figure 7:
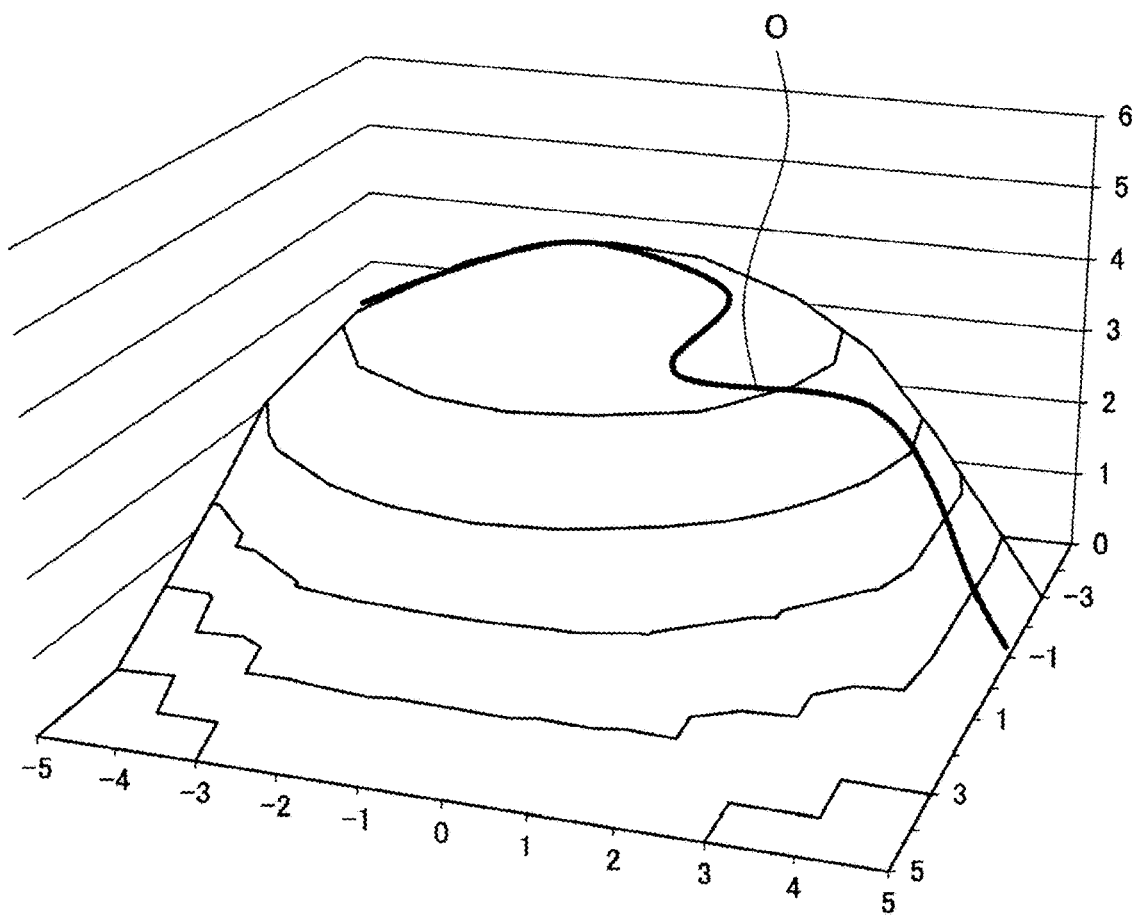
FIG. 7 is an explanatory drawing illustrating an example of "display combining a three-dimensional model with a right-eye special light observation image and a left-eye special light observation image" according to the present embodiment.

FIG. 7 is an explanatory drawing illustrating an example of the "display combining the three-dimensional model with the right-eye special light observation image and the left-eye special light observation image" according to the present embodiment. Similarly to the letter "0" in FIG. 6, the letter "0" in FIG. 7 indicates the blood vessel that is present in the surgery site (the lesion) of the observed object. In other words, FIG. 7 illustrates an example in which the blood vessel detected from the right-eye special light observation image and the left-eye special light observation image is superimposed on the three-dimensional model generated from the right-eye medical captured image and the left-eye medical captured image taken of the observed object illustrated in FIG. 6. In this situation, the method for superimposing the blood vessel detected from the special light observation images on the three-dimensional model is not particularly limited. For instance, as illustrated in the example in FIG. 7, a display screen displays the result of combining the three-dimensional model with the right-eye special light observation image and the left-eye special light observation image. Accordingly, medical providers who view the image illustrated in FIG. 7 is able to easily identify the position of the blood vessel in the observed object. Needless to say, possible examples of the "display combining a three-dimensional model with a right-eye special light observation image and a left-eye special light observation image" are not limited to the example illustrated in FIG. 7.

Possible processes related to the first application example are not limited to the example described above.

For example, when displaying a medical captured image on a display screen, the medical observation apparatus 100 may cause the position of the blood vessel superimposed on the three-dimensional model to be reflected in the medical captured image. For example, by combining the result of combining the three-dimensional model with the right-eye special light observation image and the left-eye special light observation image as illustrated in FIG. 7, with a position identified by a navigation apparatus (a medical device to realize a so-called medical navigation system), the medical observation apparatus 100 may cause the position of the blood vessel superimposed on the three-dimensional model to be reflected in the medical captured image.

[3-2] A second application example of the display controlling method according to the present embodiment: A first example of the display combining a three-dimensional model with biological information As an example of display combining a three-dimensional model with biological information, the following will describe an example in which the biological information acquiring apparatus is a nerve monitoring apparatus. When the biological information acquiring apparatus is a nerve monitoring apparatus, the biological information indicates a measured value in each of the measuring positions of the nerve monitoring apparatus.

For example, the nerve monitoring apparatus is an apparatus configured to identify the position of a nerve, by detecting an electric current level flowing between a monopolar (unipolar) electrode and a reference electrode. For example, the monopolar electrode is pressed against a region from which a nerve is to be detected. By causing an electric current for stimulating the nerve to flow from the monopolar electrode, the position of the nerve that is present in the region is identified. Needless to say, possible nerve identifying methods that can be used by the nerve monitoring apparatus are not limited to the example described above.

Figure 8:
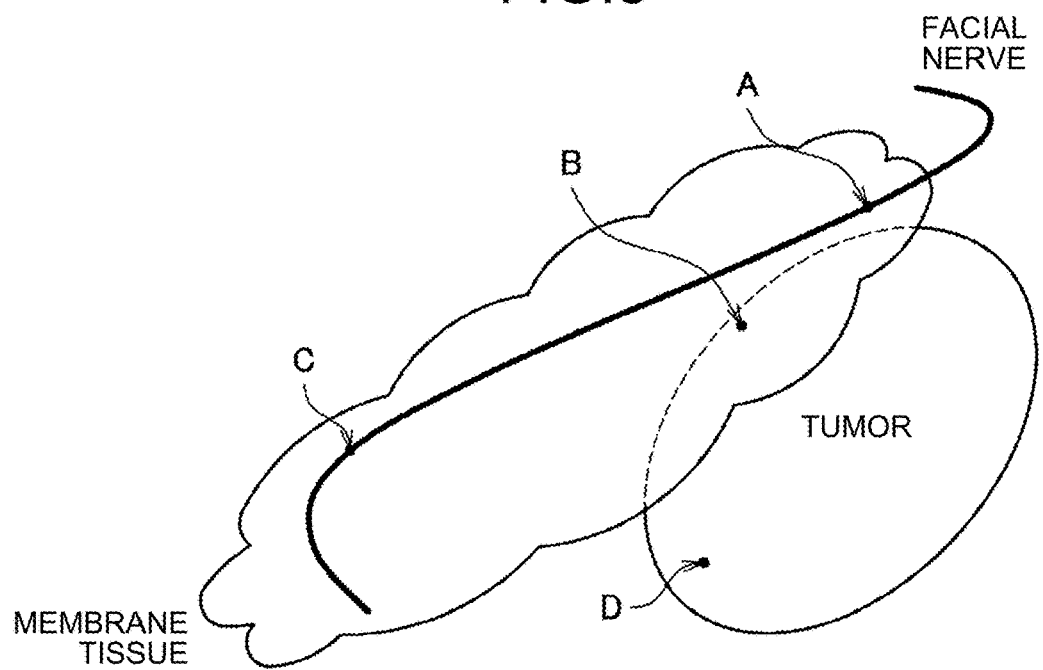
FIG. 8 is an explanatory drawing for explaining an example of a biological information acquiring process performed by a nerve monitoring apparatus.

FIGS. 8 and 9 are explanatory drawings for explaining examples of a biological information acquiring process performed by the nerve monitoring apparatus. FIG. 8 illustrates a person's face as an example of the region from which a nerve is to be detected. The points A, B, C, and D illustrated in FIG. 8 are the positions against which the monopolar electrode is pressed and correspond to the measuring positions of the nerve monitoring apparatus. Chart A in FIG. 9 indicates an example of measured values in measuring position A in FIG. 8. Chart B in FIG. 9 indicates an example of measured values in measuring position B in FIG. 8. Chart C in FIG. 9 indicates an example of measured values in measuring position C in FIG. 8. Chart D in FIG. 9 indicates an example of measured values in measuring position D in FIG. 8.

The medical observation apparatus 100 is configured to generate a three-dimensional model of an observed object from the right-eye medical captured image and the left-eye medical captured image taken of the observed object.

When the three-dimensional model has been generated, the medical observation apparatus 100 combines the three-dimensional model with an index (hereinafter, "first index") indicating a possibility of a nerve being present based on the measured values in each of the measuring positions.

Based on the right-eye medical captured image and the left-eye medical captured image, the medical observation apparatus 100 identifies the measuring positions by detecting a device corresponding to the biological information acquiring apparatus.

When the biological information acquiring apparatus is a nerve monitoring apparatus, examples of the device corresponding to the biological information acquiring apparatus include a monopolar electrode. For example, by performing a process related to an arbitrary object recognition technique for recognizing an object from an image, the medical observation apparatus 100 detects the monopolar electrode from the medical captured images. Further, the medical observation apparatus 100 identifies the part in which the detected monopolar electrode is (or is estimated to be) in contact with the observed object, as the measuring position. Needless to say, possible methods for identifying the measuring position are not limited to the example described above.

In this situation, the first index based on the measured value may be, for example, a reaction level of the nerve that is classified based on a comparison result between the measured value and one or more threshold values. Possible examples of the first index based on the measured value are not limited to the reaction level described above. For instance, the first index based on the measured value may be the measured value itself. The following will describe an example in which the first index based on the measured value is the reaction level.

For example, the medical observation apparatus 100 realizes display combining the three-dimensional model with the biological information, by causing the first index in each of the measuring positions to be displayed over the three-dimensional model. For example, by superimposing a display object corresponding to the first index in each of the measuring positions on the three-dimensional model, the medical observation apparatus 100 realizes the display combining the three-dimensional model with the biological information. In this situation, the method for superimposing the display object on the three-dimensional model is not particularly limited.

Further, the medical observation apparatus 100 may estimate the position of the nerve based on the measured values in each of the measuring positions and may cause a display screen to display a result of further combining the estimated position of the nerve. For example, by superimposing a display object indicating the estimated position of the nerve on the three-dimensional model, the medical observation apparatus 100 realizes the display combining the three-dimensional model with the estimated position of the nerve.

The position of the nerve is estimated, for example, by identifying the reaction level in each of the measuring positions and identifying a line (a straight line or a curve) that minimizes the distance to the measuring position corresponding to a measured value of a reaction level having a high possibility of a nerve being present. Needless to say, possible methods for estimating the position of the nerve based on the measured values in each of the measuring positions are not limited to the example described above. In the following sections, the result of estimating the position of the nerve based on the measured values in each of the measuring positions may be referred to as a "nerve position prediction line".

Figure 10:
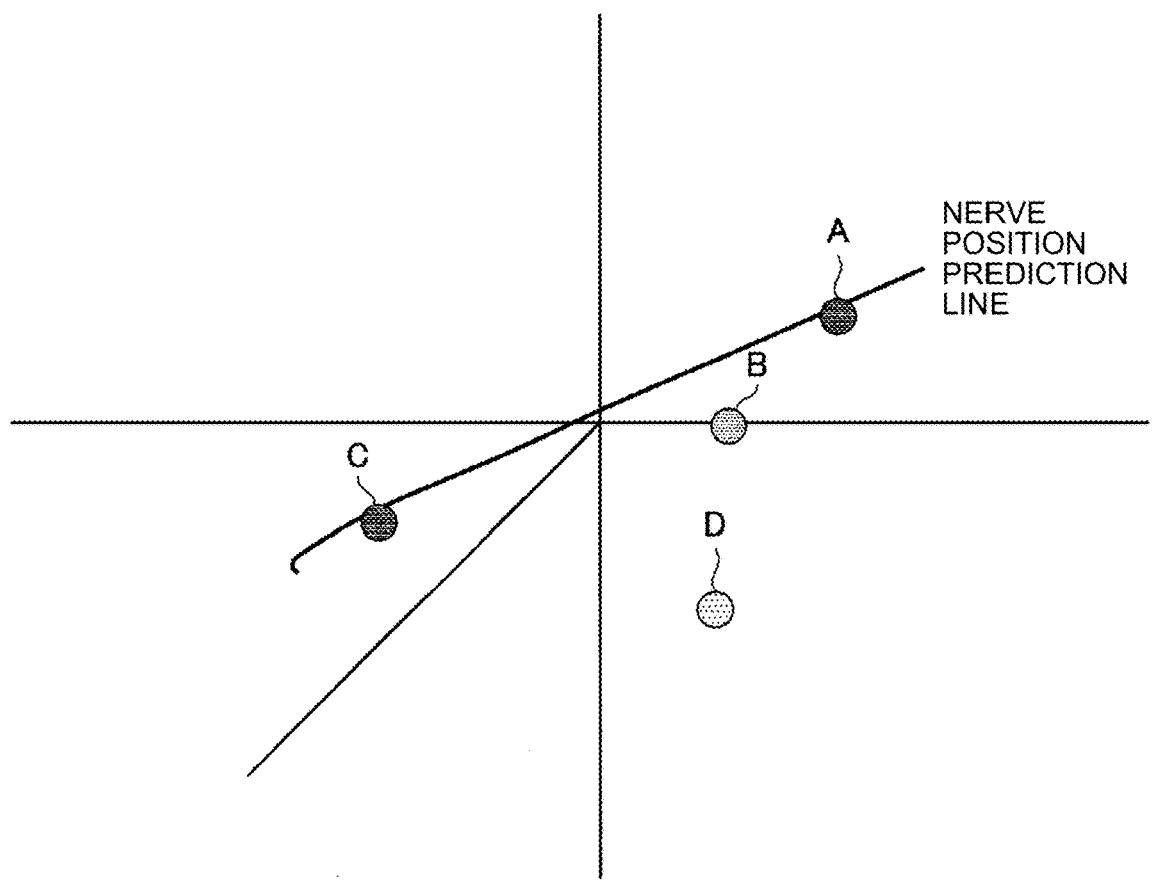
FIG. 10 is an explanatory drawing illustrating a first example of "display combining a three-dimensional model with biological information" related to a second application example of a display controlling method according to the present embodiment.

FIG. 10 is an explanatory drawing illustrating a first example of the "display combining the three-dimensional model with the biological information" related to the second application example of the display controlling method according to the present embodiment. The letter "A" in FIG. 10 indicates an example of the display object corresponding to the first index corresponding to measuring position A in FIG. 8. The letter "B" in FIG. 10 indicates an example of the display object corresponding to the first index corresponding to measuring position B in FIG. 8. The letter "C" in FIG. 10 indicates an example of the display object corresponding to the first index corresponding to measuring position C in FIG. 8. The letter "D" in FIG. 10 indicates an example of the display object corresponding to the first index corresponding to measuring position D in FIG. 8. Further, FIG. 10 illustrates the example in which a display object indicating the nerve position prediction line (a display object indicating the estimated position of the nerve) is further displayed.

For instance, as illustrated in the example in FIG. 10, a display screen displays a result of combining the three-dimensional model with the biological information acquired from the nerve monitoring apparatus. Accordingly, medical providers who view the image illustrated in FIG. 10 are able to easily identify the position of the nerve in the observed object.

Possible examples of the "display combining a three-dimensional model with biological information acquired from a nerve monitoring apparatus" are not limited to the example illustrated in FIG. 10.

For example, the "display combining a three-dimensional model with biological information" according to the second application example does not necessarily have to display the display object indicating the nerve position prediction line.

Further, for example, the medical observation apparatus 100 may further cause the display screen to display the right-eye medical captured image and the left-eye medical captured image. Alternatively, the medical observation apparatus 100 may cause the display screen to further display one of the right-eye and the left-eye medical captured images.

Figure 11:
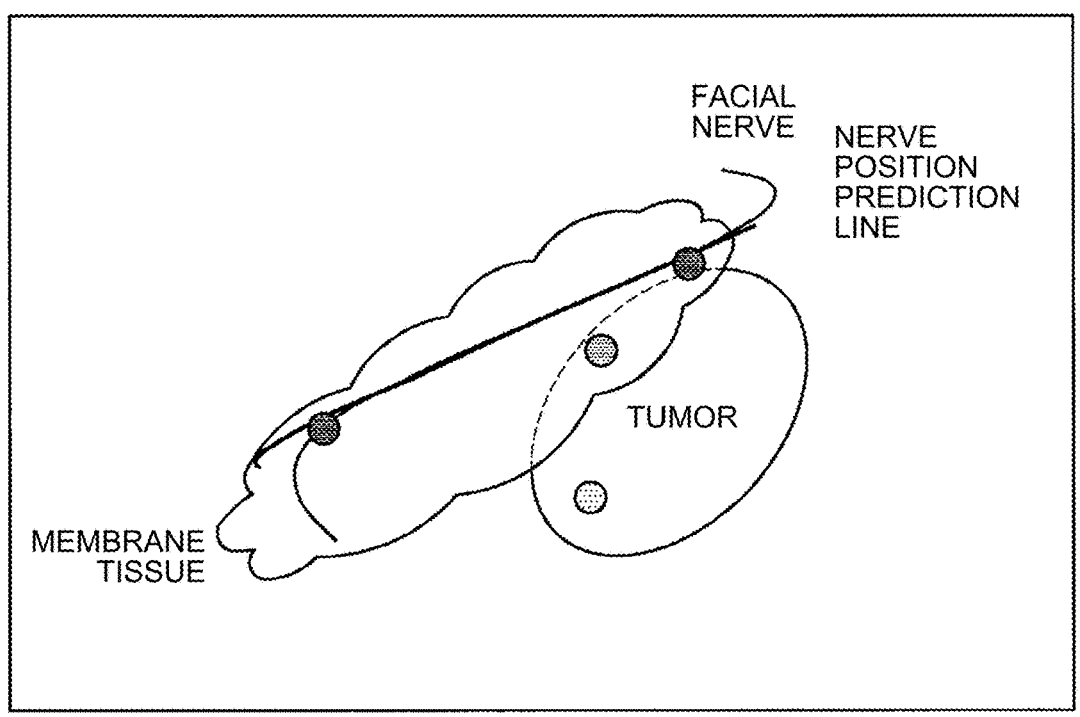
FIG. 11 is an explanatory drawing illustrating a second example of the "display combining a three-dimensional model with biological information" related to the second application example of the display controlling method according to the present embodiment.

FIG. 11 is an explanatory drawing illustrating a second example of the "display combining the three-dimensional model with the biological information" related to the second application example of the display controlling method according to the present embodiment. FIG. 11 illustrates the example in which the three-dimensional model, the display object corresponding to the first index in each of the measuring positions, and the display object indicating the nerve position prediction line illustrated in FIG. 10 are superimposed on the right-eye medical captured image and the left-eye medical captured image taken of the observed object illustrated in FIG. 8.

For example, as illustrated in FIG. 11, the medical observation apparatus 100 causes the display screen to display a result of superimposing the three-dimensional model, the display object corresponding to the first index in each of the measuring positions, and the display object indicating the nerve position prediction line, on the right-eye medical captured image and the left-eye medical captured image. As explained above, the "display combining the three-dimensional model with the biological information" according to the second application example does not necessarily have to display the display object indicating the nerve position prediction line.

Figure 12:
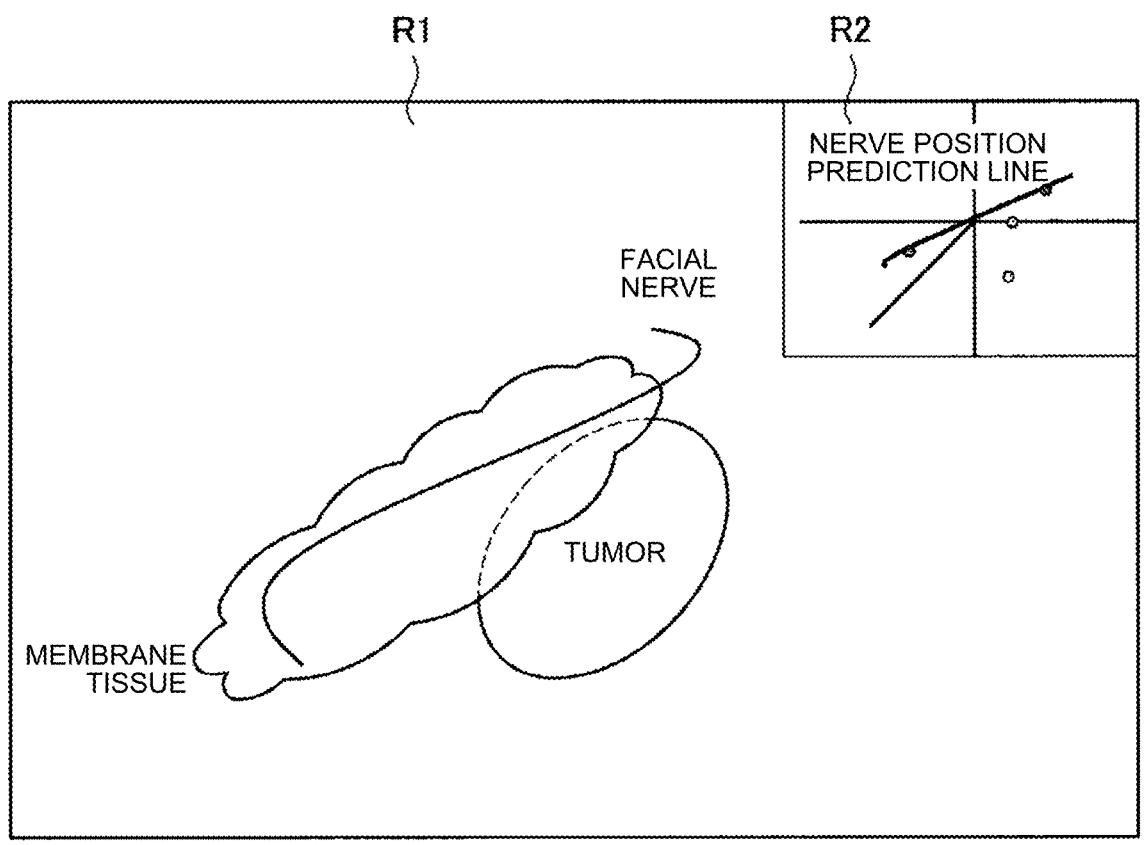
FIG. 12 is an explanatory drawing illustrating a third example of the "display combining a three-dimensional model with biological information" related to the second application example of the display controlling method according to the present embodiment.

FIG. 12 is an explanatory drawing illustrating a third example of the "display combining the three-dimensional model with the biological information" related to the second application example of the display controlling method according to the present embodiment. FIG. 12 illustrates the example in which a first region R1 of the display screen displays the right-eye medical captured image and the left-eye medical captured image taken of the observed object illustrated in FIG. 8. Further, FIG. 12 illustrates the example in which a second region R2 of the display screen displays the three-dimensional model, the display object corresponding to the first index in each of the measuring positions, and the display object indicating the nerve position prediction line illustrated in FIG. 10.

For example, as illustrated in FIG. 12, the medical observation apparatus 100 causes the right-eye medical captured image and the left-eye medical captured image to be displayed in the first region R1. Further, the medical observation apparatus 100 causes the three-dimensional model, the display object corresponding to the first index in each of the measuring positions, and the display object indicating the nerve position prediction line to be displayed in the second region R2 different from the first region R1. As explained above, the "display combining the three-dimensional model with the biological information" according to the second application example does not necessarily have to display the display object indicating the nerve position prediction line.

In the example illustrated in FIG. 12, the second region R2 is displayed by using Picture in Picture (P in P). However, possible methods for displaying the second region R2 are not limited to the example in FIG. 12. For instance, the medical observation apparatus 100 may divide the display screen into regions so that mutually-different regions among the regions resulting from the division are designated as the first region R1 and the second region R2.

[3-3] A third application example of the display controlling method according to the present embodiment: a second example of the display combining a three-dimensional model with biological information As another example of the display combining a three-dimensional model with biological information, an example will be explained in which the biological information acquiring apparatus is a nerve stimulation apparatus configured to electrically stimulate the vagus nerve.

For example, the nerve stimulation apparatus is an apparatus configured to output a stimulation pulse (an electrical pulse) to the vagus nerve, via an electrode pressed against a region of the heart to which the electrical stimulation is to be applied, so as to detect heartbeats of the heart. The position against which the electrode is pressed corresponds to a measuring position of the nerve stimulation apparatus. The nerve stimulation apparatus configured to electrically stimulate the vagus nerve may be referred to as a pacing analyzer.

FIG. 13 is an explanatory drawing for explaining an example of a biological information acquiring process performed by a nerve stimulation apparatus. Chart A in FIG. 13 indicates an example of biological information acquired by the nerve stimulation apparatus in one measuring position. Chart B in FIG. 13 indicates an example of biological information acquired by the nerve stimulation apparatus in another measuring position. When the biological information acquiring apparatus is a nerve stimulation apparatus, the biological information includes a stimulation threshold value. In this situation, the stimulation threshold value is a value of threshold voltage at the time when a stimulation pulse being output has a pulse width that minimizes the energy of the stimulation pulse applied to the vagus nerve.

The medical observation apparatus 100 generates a three-dimensional model of the observed object, from a right-eye medical captured image and a left-eye medical captured image taken of the observed object.

When the three-dimensional model has been generated, the medical observation apparatus 100 combines the three-dimensional model with an index (hereinafter, "second index") of the stimulation threshold value in each of the measuring positions.

Similarly to the second application example above, the medical observation apparatus 100 identifies the measuring positions, by detecting a device corresponding to the biological information acquiring apparatus, based on the right-eye medical captured image and the left-eye medical captured image.

When the biological information acquiring apparatus is a nerve stimulation apparatus, examples of the device corresponding to the biological information acquiring apparatus include the electrode configured to output the stimulation pulse. For example, by performing a process related to an arbitrary object recognition technique for recognizing an object from an image, the medical observation apparatus 100 detects the electrode configured to output the stimulation pulse from the medical captured images. Further, the medical observation apparatus 100 identifies the part in which the detected electrode configured to output the stimulation pulse is (or is estimated to be) in contact with the observed object, as the measuring position. Needless to say, possible methods for identifying the measuring position are not limited to the example described above.

In this situation, the second index may be, for example, a level of the stimulation threshold value classified based on a comparison result between the stimulation threshold value and one or more judgment threshold values. Possible examples of the second index are not limited to the level of the stimulation threshold value described above. For instance, the second index may be the stimulation threshold value itself. The following will describe an example in which the second index is the level of the stimulation threshold value.

For example, the medical observation apparatus 100 realizes display combining the three-dimensional model with the biological information, by causing the second index in each of the measuring positions to be displayed over the three-dimensional model. For example, the medical observation apparatus 100 realizes the display combining the three-dimensional model with the biological information by superimposing, on the three-dimensional model, a display object corresponding to the second index in each of the measuring positions.

Figure 14:
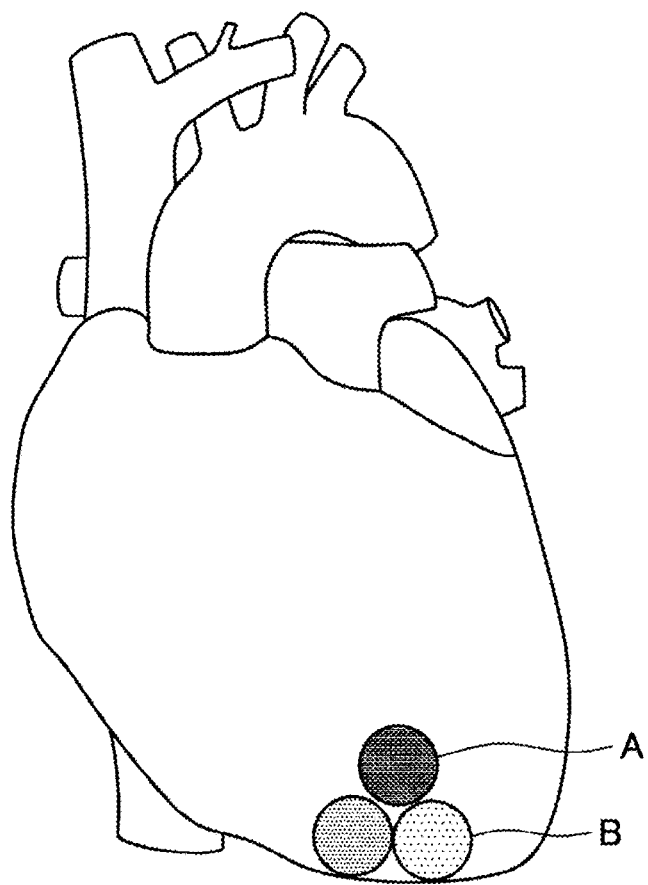
FIG. 14 is an explanatory drawing illustrating an example of "display combining a three-dimensional model with biological information" related to a third application example of the display controlling method according to the present embodiment.

FIG. 14 is an explanatory drawing illustrating an example of the "display combining a three-dimensional model with biological information" related to a third application example of the display controlling method according to the present embodiment. In FIG. 14, the letter "A" indicates an example of the display object corresponding to the second index in the measuring position corresponding to chart A in FIG. 13. In FIG. 14, the letter "B" indicates an example of the display object corresponding to the second index in the measuring position corresponding to chart B in FIG. 13. In addition, FIG. 14 also illustrates an example of the display object corresponding to the second index in another measuring position.

For example, as illustrated in the example in FIG. 14, a display screen displays a result of combining the three-dimensional model with the biological information acquired from the nerve stimulation apparatus. Accordingly, as illustrated in the example in FIG. 14, a reaction level to the stimulation pulse in each of the positions of the electrode configured to output the stimulation pulse is simultaneously displayed with a myocardial model expressed as the three-dimensional model. Consequently, medical providers who view the image illustrated in FIG. 14 are able to determine more easily the minimum voltage required to move the myocardia.

Possible examples of the "display combining a three-dimensional model with biological information acquired from a nerve stimulation apparatus" are not limited to the example illustrated in FIG. 14. For instance, the medical observation apparatus 100 may further cause the biological information in each of the measuring positions illustrated in FIG. 13 to be displayed.

Processes related to the third application example are not limited to the example described above.

For example, as explained above, the medical observation apparatus 100 is also capable of causing three-dimensional models generated at different points in time during a predetermined time period to be sequentially displayed in a time series. As explained above, as a result of the three-dimensional models being sequentially displayed in the time series, the three-dimensional model also moves in accordance with moves of the observed object in the predetermined time period. Accordingly, the viewer of the display screen is able to recognize, from the three-dimensional models, the moves of the observed object in the predetermined time period.

FIG. 15 is an explanatory drawing illustrating an example of the processes related to the third application example of the display controlling method according to the present embodiment. The letter "A" in FIG. 15 indicates an example of a three-dimensional model generated at a first point in time. The letter "B" in FIG. 15 indicates an example of a three-dimensional model generated at a second point in time (which is later than the first point in time).

For example, as a result of the three-dimensional model "A" in FIG. 15 and the three-dimensional model "B" in FIG. 15 being sequentially displayed in a time series, the viewer of the display screen is able to recognize, from the three-dimensional models, moves of the observed object in the predetermined time period.

Further, for example, as explained above, the medical observation apparatus 100 may record, on an arbitrary recording medium such as a recording medium (not illustrated) that functions as a storage unit (not illustrated), the three-dimensional model and other data besides the three-dimensional model, so as to be kept in correspondence with each other by using an arbitrary method. In the third application example, for instance, the medical observation apparatus 100 is configured to record a part or all of the following so as to be kept in correspondence with the three-dimensional model: data indicating the measuring positions of the nerve stimulation apparatus; data indicating a stimulation threshold value in each of the measuring positions; data indicating moves of the observed object expressed with numerical values; and data indicating the special light observation images.

Possible application examples of the display controlling method according to the present embodiment include the first to the third application examples presented above in sections [3-1] to [3-3]. Needless to say, possible processes performed in the application examples described in sections [3-1] to [3-3] are not limited to the examples described above, and possible application examples of the display controlling method according to the present embodiment are not limited to the application examples described in sections [3-1] to [3-3] above.

[4] Examples of advantageous effects achieved by using the display controlling method according to the present embodiment By using the display controlling method according to the present embodiment, the following advantageous effects are achieved, for example. Needless to say, possible advantageous effects achieved by the display controlling method according to the present embodiment are not limited to the following examples.

In addition to simply acquiring three-dimensional white-light images (the medical captured images taken by using natural light) and the special light observation images by imaging the imaged subject ("the observed object"; the same applies hereinafter), the model of three dimensions ("three-dimensional model"; the same applies hereinafter) is generated during the surgery. Accordingly, medical providers such as the practitioner are able to understand the size and the position of the imaged subject in units of millimeters [mm]. Consequently, by using the display controlling method according to the present embodiment, it is possible to assist the medical providers in understanding the anatomy.

It is possible to express, with numerical values, the shape of the imaged subject after the surgery (e.g., after exfoliation, incision, or anastomosis) and the flowing direction and velocity of blood flows which cannot be visually perceived. It is therefore possible to judge the quality of the surgery after the surgery.

Because the biological information of the imaged subject acquired from the external biological information acquiring apparatus is brought into collaboration with the data of the model of three dimensions, medical providers are able to achieve a detailed understanding of the anatomy.

For example, when a nerve stimulation apparatus configured to electrically stimulate the vagus nerve is used for setting a stimulation value of a heart pacemaker, motion of the heart changes depending on myocardial stimulation values (the values of the stimulation pulse) of the nerve stimulation apparatus. In this situation, by using the display controlling method according to the present embodiment, it is possible to display, with numerical values, the changes in the motion of the heart occurring between before and after the surgery. It is therefore possible to assist the medical providers in judging the quality of the surgery.

<Computer programs according to the present embodiment>

When a processor or the like in a computer system executes a computer program (e.g., a program capable of executing the processes related to the display controlling method according to the present embodiment) configured to cause the computer system to function as the medical observation apparatus according to the present embodiment (or the medical display controlling apparatus according to the present embodiment), it is possible to enhance the convenience of medical providers. In this situation, possible examples of the computer system according to the present embodiment include a stand-alone computer and a plurality of computers. The computer system according to the present embodiment is configured to perform the series of processes related to the display controlling method according to the present embodiment.

Further, when a processor or the like in a computer system executes a computer program configured to cause the computer system to function as the medical observation apparatus according to the present embodiment (or the medical display controlling apparatus according to the present embodiment), it is possible to achieve the abovementioned advantageous effects exerted by the display realized with the processes related to the display controlling method according to the present embodiment.

Some of the preferred embodiments of the present disclosure have thus been explained in detail, with reference to the accompanying drawings; however, the technical scope of the present disclosure is not limited to the above examples. It is apparent that a person having ordinary knowledge in the technical field of the present disclosure is able to conceive of various modification examples and revised examples within the scope of the technical concept set forth in the claims. It is therefore understood that those examples also naturally fall in the technical scope of the present disclosure.

For instance, the above example describes providing the program (the computer program) that causes the computer system to function as the medical observation apparatus according to the present embodiment (or the medical display controlling apparatus according to the present embodiment). In addition, the present embodiment is also able to provide a recording medium that has the program stored therein.

The configurations presented above are merely examples of the present embodiments and naturally fall in the technical scope of the present disclosure.

Further, the advantageous effects set forth in the present description are merely explanatory and illustrative, but are not restrictive. In other words, the features of the present disclosure may achieve other advantageous effects that are obvious to a person skilled in the art from the present description, in addition to, or in place of, the abovementioned advantageous effects.

The following configurations also fall in the technical scope of the present disclosure:

(1)
A medical display controlling apparatus including:
a generating unit configured to generate a three-dimensional model of an observed object based on a right-eye medical captured image and a left-eye medical captured image taken by an imaging device configured to image the observed object; and
a display controller configured to cause a display screen to display:
a combination of the three-dimensional model and a right-eye special light observation image and a left-eye special light observation image; or
a combination of the three-dimensional model and biological information acquired from an external biological information acquiring apparatus.

(2)
The medical display controlling apparatus according to (1), wherein
the display controller corrects a distance calculated from the right-eye special light observation image and the left-eye special light observation image by using a distance calculated from the right-eye medical captured image and the left-eye medical captured image, and
the display controller combines the three-dimensional model with the right-eye special light observation image and the left-eye special light observation image based on a result of the correction made on the distance calculated from the right-eye special light observation image and the left-eye special light observation image.

(3)
The medical display controlling apparatus according to (1), wherein
the biological information acquiring apparatus is a nerve monitoring apparatus,
the biological information indicates a measured value in each of measuring positions of the nerve monitoring apparatus, and
the display controller causes the display screen to display a combination of the three-dimensional model and an index indicating a possibility of a nerve being present based on the measured value in each of the measuring positions.

(4)
The medical display controlling apparatus according to (3), wherein the display controller causes the index in each of the measuring positions to be displayed over the three-dimensional model.

(5)
The medical display controlling apparatus according to (3) or (4), wherein
the display controller estimates a position of the nerve based on the measured value in each of the measuring positions, and
the display controller causes the display screen to display the combination by further combining the estimated position of the nerve.

(6)
The medical display controlling apparatus according to (5), wherein the display controller causes the estimated position of the nerve to be displayed over the three-dimensional model.

(7)
The medical display controlling apparatus according to any one of (3) to (6), wherein the display controller causes the display screen to further display the right-eye medical captured image and the left-eye medical captured image.

(8)
The medical display controlling apparatus according to (7), wherein the display controller causes the display screen to display a result of superimposing the three-dimensional model and the index in each of the measuring positions on the right-eye medical captured image and the left-eye medical captured image.

(9)
The medical display controlling apparatus according to (7), wherein
the display controller causes the right-eye medical captured image and the left-eye medical captured image to be displayed in a first region of the display screen, and
the display controller causes a combination of the three-dimensional model and the index in each of the measuring positions to be displayed in a second region of the display screen that is different from the first region.

(10)
The medical display controlling apparatus according to (1), wherein
the biological information acquiring apparatus is a nerve stimulation apparatus configured to electrically stimulate a vagus nerve,
the biological information includes a stimulation threshold value, and
the display controller causes the display screen to display a combination of the three-dimensional model and an index of the stimulation threshold value in each of measuring positions of the nerve stimulation apparatus.

(11)
The medical display controlling apparatus according to (10), wherein the display controller causes the index of the stimulation threshold value in each of the measuring positions to be displayed over the three-dimensional model.
(12)
The medical display controlling apparatus according to any one of (3) to (11), wherein the display controller identifies the measuring positions by detecting a device corresponding to the biological information acquiring apparatus, based on the right-eye medical captured image and the left-eye medical captured image.
(13)
The medical display controlling apparatus according to any one of (1) to (12), wherein the display controller causes the three-dimensional model generated at each of points in time during a predetermined time period to be sequentially displayed in a time series.
(14)
The medical display controlling apparatus according to any one of (1) to (13), wherein the biological information is information corresponding to an anatomical structure.
(15)
The medical display controlling apparatus according to any one of (1) to (14), further including:
an arm configured by connecting a plurality of links to one another with joint parts; and
the imaging device supported by the arm.
(16)
The medical display controlling apparatus according to any one of (1) to (14), further including: the imaging device configured to be inserted into an inside of a body of a patient, so as to image the inside of the body as the observed object.
(17)
A display controlling method implemented by a medical display controlling apparatus, the display controlling method including:
generating a three-dimensional model of an observed object based on a right-eye medical captured image and a left-eye medical captured image taken by an imaging device configured to image the observed object; and
causing a display screen to display a combination of the three-dimensional model and a right-eye special light observation image and a left-eye special light observation image, or causing the display screen to display a combination of the three-dimensional model with biological information acquired from an external biological information acquiring apparatus.

REFERENCE SIGNS LIST

100 MEDICAL OBSERVATION APPARATUS
102 BASE
104 ARM
106 IMAGING DEVICE
110*a*, 110*b*, 110*c*, 110*d*, 110*e*, 110*f* JOINT PART
112*a*, 112*b*, 112*c*, 112*d*, 112*e*, 112*f* LINK
120 IMAGING MEMBER
122 CYLINDRICAL MEMBER
124 ZOOM SWITCH
126 FOCUS SWITCH
128 OPERATION MODE CHANGING SWITCH
134 INSERTION MEMBER
136 LIGHT SOURCE UNIT
138 LIGHT GUIDE
140 CAMERA HEAD
142 CABLE
144 CONTROLLING UNIT
150 IMAGING UNIT
152 COMMUNICATION UNIT
154 CONTROL UNIT
156 IMAGING CONTROLLER
158 GENERATING UNIT
160 DISPLAY CONTROLLER
200 DISPLAY DEVICE
1000 MEDICAL OBSERVATION SYSTEM

The invention claimed is:
1. A medical display controlling apparatus comprising:
a generating circuit configured to generate a three-dimensional model of an observed object based on a right-eye medical captured image and a left-eye medical captured image taken by an imaging device configured to image the observed object; and
a display control circuit configured to:
correct a distance calculated from a right-eye special light observation image and a left-eye special light observation image by using a distance calculated from the right-eye medical captured image and the left-eye medical captured image, and
combine the three-dimensional model and the right-eye special light observation image and the left-eye special light observation image having the corrected distance; and
cause a display screen to display the combination.
2. The medical display controlling apparatus according to claim 1, wherein the display control circuit is configured to cause the display screen to further display the right-eye medical captured image and the left-eye medical captured image.
3. The medical display controlling apparatus according to claim 2, wherein the display control circuit is configured to cause the display screen to display a result of superimposing the three-dimensional model and the index in each of the measuring positions on the right-eye medical captured image and the left-eye medical captured image.
4. The medical display controlling apparatus according to claim 2, wherein
the display control circuit is configured to cause the right-eye medical captured image and the left-eye medical captured image to be displayed in a first region of the display screen, and
the display control circuit is configured to cause a combination of the three-dimensional model and the index in each of the measuring positions to be displayed in a second region of the display screen that is different from the first region.
5. The medical display controlling apparatus according to claim 1, wherein the display control circuit is configured to cause the three-dimensional model generated at each of points in time during a predetermined time period to be sequentially displayed in a time series.
6. The medical display controlling apparatus according to claim 1, wherein the biological information is information corresponding to an anatomical structure.
7. The medical display controlling apparatus according to claim 1, further comprising:
an arm configured by connecting a plurality of links to one another with joint parts; and
the imaging device supported by the arm.
8. The medical display controlling apparatus according to claim 1, wherein the imaging device configured to be inserted into an inside of a body of a patient to image the inside of the body as the observed object.

9. A display controlling method implemented by a medical display controlling apparatus, the display controlling method comprising:
- generating a three-dimensional model of an Observed object based on a right-eye medical captured image and a left-eye medical captured image taken by an imaging device configured to image the observed object;
- correcting a distance calculated from a right-eye special light observation image and a left-eye special light observation image by using a distance calculated from the right-eye medical captured image and the left-eye medical captured image,
- combining the three-dimensional model and the right-eye special light observation image and the left-eve special light observation image having the corrected distance; and
- causing a display screen to display the combination.

10. A medical display controlling apparatus comprising:
- a generating circuit configured to generate a three-dimensional model of an observed object based on a right-eye medical captured image and a left-eye medical captured image taken by an imaging device configured to image the observed object; and
- a display control circuit configured to cause a display screen to display:
  - a combination of the three-dimensional model and biological information acquired from an external biological information acquiring apparatus; and
  - the right-eye medical captured image and the left-eye medical captured image.

11. The medical display controlling apparatus according to claim 10, wherein
- the biological information acquiring apparatus is a nerve monitoring apparatus,
- the biological information indicates a measured value in each of measuring positions of the nerve monitoring apparatus, and
- the display control circuit is configured to cause the display screen to display a combination of the three-dimensional model and an index indicating a possibility of a nerve being present based on the measured value in each of the measuring positions.

12. The medical display controlling apparatus according to claim 11, wherein the display control circuit is configured to cause the index in each of the measuring positions to be displayed over the three-dimensional model.

13. The medical display controlling apparatus according to claim 11, wherein
- the display control circuit is configured to estimate a position of the nerve based on the measured value in each of the measuring positions, and
- the display control circuit is configured to cause the display screen to display the combination by further combining the estimated position of the nerve.

14. The medical display controlling apparatus according to claim 13, wherein the display control circuit is configured to cause the estimated position of the nerve to be displayed over the three-dimensional model.

15. The medical display controlling apparatus according to claim 11, wherein the display control circuit is configured to identify the measuring positions by detecting a device corresponding to the biological information acquiring apparatus, based on the right-eye medical captured image and the left-eye medical captured image.

16. The medical display controlling apparatus according to claim 10, wherein
- the biological information acquiring apparatus is a nerve stimulation apparatus configured to electrically stimulate a vagus nerve,
- the biological information includes a stimulation threshold value, and
- the display control circuit is configured to cause the display screen to display a combination of the three-dimensional model and an index of the stimulation threshold value in each of measuring positions of the nerve stimulation apparatus.

17. The medical display controlling apparatus according to claim 16, wherein the display control circuit is configured to cause the index of the stimulation threshold value in each of the measuring positions to be displayed over the three-dimensional model.

18. The medical display controlling apparatus according to claim 10, wherein the display control circuit is configured to cause the display screen to display a result of superimposing the three-dimensional model and the index in each of the measuring positions on the right-eye medical captured image and the left-eye medical captured image.

19. The medical display controlling apparatus according to claim 10, wherein
- the display control circuit is configured to cause the right-eye medical captured image and the left-eye medical captured image to be displayed in a first region of the display screen, and
- the display control circuit is configured to cause a combination of the three-dimensional model and the index in each of the measuring positions to be displayed in a second region of the display screen that is different from the first region.

20. The medical display controlling apparatus according to claim 10, further comprising:
- an arm configured by connecting a plurality of links to one another with joint parts; and
- the imaging device supported by the arm.

* * * * *